US012135328B2

(12) United States Patent
Mao et al.

(10) Patent No.: US 12,135,328 B2
(45) Date of Patent: *Nov. 5, 2024

(54) TANDEM MASS TAG MULTIPLEXED QUANTITATION OF POST-TRANSLATIONAL MODIFICATIONS OF PROTEINS

(71) Applicant: Regeneron Pharmaceuticals, Inc., Tarrytown, NY (US)

(72) Inventors: Yuan Mao, Hartsdale, NY (US); Andrew Kleinberg, Roslyn Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 44 days.

This patent is subject to a terminal disclaimer.

(21) Appl. No.: 18/123,753

(22) Filed: Mar. 20, 2023

(65) Prior Publication Data

US 2023/0349916 A1 Nov. 2, 2023

Related U.S. Application Data

(63) Continuation of application No. 17/159,136, filed on Jan. 26, 2021, now Pat. No. 11,639,939.

(Continued)

(51) Int. Cl.
*G01N 33/68* (2006.01)
*G01N 30/72* (2006.01)
*G01N 30/02* (2006.01)

(52) U.S. Cl.
CPC ..... *G01N 33/6848* (2013.01); *G01N 30/7233* (2013.01); *G01N 2030/027* (2013.01); *G01N 2458/15* (2013.01)

(58) Field of Classification Search
None
See application file for complete search history.

(56) References Cited

U.S. PATENT DOCUMENTS 11,639,939 B2 5/2023 Mao et al.
2020/0033361 A1 1/2020 Dai et al.

FOREIGN PATENT DOCUMENTS

WO 18/170981 A1 9/2018

OTHER PUBLICATIONS

WIPO Application No. PCT/US2021/015146, PCT International Search Report and Written Opinion of the International Searching Authority mailed Jun. 4, 2021.

(Continued)

*Primary Examiner* — Xiaoyun R Xu
(74) *Attorney, Agent, or Firm* — Schwabe, Williamson & Wyatt P.C.; David Mellman

(57) ABSTRACT

Disclosed are methods of quantifying multiple quality attributes, such as post translational modifications, of multiple samples in a single mass spectrometry (MS) run, including contacting two or more samples with a digesting solution under conditions sufficient to digest samples, wherein each sample is digested separately and the digesting solution is a Tris-free buffer solution; contacting each of the two or more digested samples with a specific Tandem Mass Tag (TMT) labeling reagent under conditions sufficient to label peptides within each of the digested samples with the specific TMT labeling reagent; quenching labeling of peptides within each of the two or more digested samples; combining equal volumes of the two or more labeled, digested samples into a single combined sample solution; and analyzing the single combined sample solution by targeted mass spectral analysis, thereby allowing multiple quality attributes of the two or more samples to be quantified in a single mass spectrometry (MS) run.

17 Claims, 16 Drawing Sheets

Specification includes a Sequence Listing.

Related U.S. Application Data

(60) Provisional application No. 62/966,151, filed on Jan. 27, 2020.

(56) References Cited

OTHER PUBLICATIONS

Aich et al., "State-of-the-art technologies for rapid and high-throughput sample preparation and analysis of N-glycans from antibodies," Electrophoresis, vol. 37 No. 11: 1468-1488, (Mar. 16, 2016). [XP055658199, ISSN: 0173-0835, DOI: 10.1002/elps.201500551].

Lu et al., "Capillary Electrophoresis Separations of Glycans," Chemical Reviews, vol. 118 No. 17: 7867-7885, (Mar. 12, 2018). [XP055659172, ISSN: 009-2665, DOI: 10.1021/acs.chemrev.7b00669].

Mao Yuan et al., "Isobaric Tandem Mass Tag Multiplexed Post-Translational Modification Quantitation of Biopharmaceuticals by Targeted High-Resolution Mass Spectrometry," Analytical Chemistry, vol. 92 No. 14: 9682-9690, (Jun. 19, 2020). [XP055806969, ISSN: 003-270, DOI: 10.1021/acs.analchem.0c00999].

Zhao et al., "Glycine additive facilitates site-specific glycosylation profiling of biopharmaceuticals by ion-pairing hydrophilic interaction chromatography mass spectrometry," Analytical and Bioanalytical Chemistry, vol. 413 No. 5: 1267-1277, (Nov. 26, 2020). [XP037373229, ISSN: 1618-2642, DOI: 10.1007/S00216-020-03089-3].

U.S. Appl. No. 17/159,136, Non-Final Office Action mailed Sep. 6, 2022.

U.S. Appl. No. 17/159,136, Notice of Allowance mailed Dec. 21, 2022.

Roy et al., "Absolute Quantitation of Glycoforms of Two Human IgG Subclasses Using Synthetic Fc Peptides and Glycopeptides," J. Am. Soc. Mass Spectrom, vol. 29:1086-1096, (2018). DOI: 10.1007/s13361-018-1900-7.

U.S. Appl. No. 62/966,151, filed Jan. 27, 2020, Expired.

PCT/US2021/015146, Jan. 26, 2021, WO 2021/154764, Published.

U.S. Appl. No. 17/159,136, filed Jan. 26, 2021.

| Peptide | # of TMT | TMT-labeled Species | Percentage of TMT-labeled Species (%) | | | | |
|---|---|---|---|---|---|---|---|
| | | | Control (No inhibitor) | BOC-Y | HPAA | HBA | PABA |
| WQQGNVFSCSVMHEALHNHYTQK (SEQ ID NO: 3) | 1 | NH2-WQQGNVFSCSVMHEALHNHYTQK | 0.2 | 1.4 | 0.1 | 0.1 | 0.3 |
| | 2 | NH2-WQQGNVFSCSVMHEALHNHYTQK | 0.0 | 3.5 | 0.0 | 0.1 | 0.9 |
| | | NH2-WQQGNVFSCSVMHEALHNHYTQK | 1.0 | 31.8 | 8.2 | 16.3 | 15.3 |
| | 3 | NH2-WQQGNVFSCSVMHEALHNHYTQK | 0.9 | 0.5 | 1.0 | 1.3 | 0.7 |
| | | NH2-WQQGNVFSCSVMHEALHNHYTQK | 3.2 | 1.2 | 3.2 | 3.7 | 2.0 |
| | | NH2-WQQGNVFSCSVMHEALHNHYTQK | 1.8 | 0.9 | 2.3 | 2.9 | 1.7 |
| | | NH2-WQQGNVFSCSVMHEALHNHYTQK | 4.2 | 56.0 | 44.2 | 49.9 | 60.9 |
| | 4 | NH2-WQQGNVFSCSVMHEALHNHYTQK | 5.1 | 0.0 | 0.9 | 0.6 | 0.2 |
| | | NH2-WQQGNVFSCSVMHEALHNHYTQK | 5.5 | 0.9 | 6.3 | 4.5 | 3.4 |
| | | NH2-WQQGNVFSCSVMHEALHNHYTQK | 17.5 | 2.1 | 16.9 | 11.4 | 8.2 |
| | | NH2-WQQGNVFSCSVMHEALHNHYTQK | 5.2 | 1.5 | 9.7 | 6.4 | 5.1 |
| | 5 | NH2-WQQGNVFSCSVMHEALHNHYTQK | 3.2 | 0.0 | 0.1 | 0.0 | 0.0 |
| | | NH2-WQQGNVFSCSVMHEALHNHYTQK | 11.5 | 0.0 | 1.6 | 0.7 | 0.3 |
| | | NH2-WQQGNVFSCSVMHEALHNHYTQK | 6.1 | 0.0 | 1.4 | 0.5 | 0.3 |
| | | NH2-WQQGNVFSCSVMHEALHNHYTQK | 22.0 | 0.0 | 3.8 | 1.5 | 0.8 |
| | 6 | NH2-WQQGNVFSCSVMHEALHNHYTQK | 12.6 | 0.0 | 0.3 | 0.1 | 0.0 |
| TTPPVLDSDGSFFLYSK (SEQ ID NO: 4) | 1 | NH2-TTPPVLDSDGSFFLYSK | 0.0 | 5.2 | 0.0 | 0.3 | 1.3 |
| | 2 | NH2-TTPPVLDSDGSFFLYSK | 0.0 | 1.5 | 0.3 | 0.8 | 0.5 |
| | | NH2-TTPPVLDSDGSFFLYSK | 0.8 | 1.1 | 1.1 | 1.1 | 1.1 |
| | | NH2-TTPPVLDSDGSFFLYSK | 73.0 | 90.5 | 91.7 | 93.5 | 93.3 |
| | 3 | NH2-TTPPVLDSDGSFFLYSK | 26.1 | 1.5 | 6.9 | 4.3 | 3.8 |

FIG.9

TANDEM MASS TAG MULTIPLEXED QUANTITATION OF POST-TRANSLATIONAL MODIFICATIONS OF PROTEINS

CROSS-REFERENCE TO RELATED APPLICATIONS

This application is a continuation of U.S. application Ser. No. 17/159,136, filed Jan. 26, 2021, which claims the benefit under 35 USC § 119(e) of U.S. Provisional Application No. 62/966,151, filed Jan. 27, 2020, each of which is incorporated herein by reference in its entirety for all purposes.

REFERENCE TO A SEQUENCE LISTING

This application incorporates by reference a computer readable Sequence Listing in ST.26 XML format, titled 10693US02_Sequence, created on Mar. 20, 2023 and containing 6,194 bytes.

FIELD OF THE INVENTION

The present invention pertains to biopharmaceuticals, and relates to a tandem mass tag (TMT) multiplexed quantitation of post-translational modifications of proteins, such as therapeutic monoclonal antibodies.

BACKGROUND

Since the first approval by the US Food and Drug Administration (FDA) in 1986, recombinant monoclonal antibodies (mAbs) have emerged as one of the most rapidly growing classes of biotherapeutics in the treatment of various human diseases in drug development pipelines and in the biopharmaceutical drug market, due to their high specificity, long circulating half-life, the possibility of invoking immune cell effector response, and fewer side effects compared to small-molecule drugs. To date, approximately 80 IgG mAbs drug products have been approved by FDA and the European Medicines Agency (EMA), and more than 70 are in late stage development.

IgG mAbs are approximately 150 kDa covalent heterotetramer proteins consisting of two identical heavy and light chains that are covalently linked through multiple disulfide bonds to form a Y-shaped structure. Due to their large size and structural complexity, mAbs are susceptible to a wide variety of post-translational modifications (PTMs) such as Fc glycosylation, methionine (Met) oxidation, asparagine (Asn) deamidation, aspartic acid (Asp) cyclization/isomerization, N-terminal glutamine (Gln) or glutamate (Glu) cyclization, C-terminal lysine (Lys) clipping, non-enzymatic Lys glycation and trisulfide bond during cell culture, purification, formulation and storage. PTMs can be the leading source of structural heterogeneity and play an important role in modulating the physiochemical properties of mAbs. Some PTMs such as glycosylation, deamidation and oxidation depending on the locations of affected residues (e.g., in complementarity-determining regions (CDRs)), may even have detrimental effects on stability, function, immunogenicity and pharmacokinetics/pharmacodynamics, which are normally considered as critical quality attributes (CQAs) of antibodies for close monitoring during the drug development (Wang et al., *J. Pharm. Sci.* 2007, 96, 1-26; Manning et al., *Pharm Res.* 2010, 27, 544-557). Oxidation of two conserved Met residues located at the interface of heavy chain constant domains 2 (CH2) and 3 (CH3) in most IgG antibodies can decrease the thermal stability (Houde et al., *Mol. Cell.* *Proteomics.* 2010, 9, 1716-1728), protein A binding (Bertolotti-Ciarlet et al., *Mol. Immunol.* 2009, 46, 1878-1882), FcRn binding (Zhang et al., *Anal. Chem.* 2014, 86, 3468-3475), and circulation half-life of IgG antibodies (Wang et al., *Mol. Immunol.* 2011, 48, 860-866), whereas Met or tryptophan (Trp) oxidation and Asn deamidation in the solvent exposed CDRs could potentially impact the antigen binding and potency (Wei et al., *J. Pharm. Sci.* 2009, 98, 3509-3521; Yan et al., *J. Pharm. Sci.* 2009, 98, 3509-3521). N-linked glycosylation at conserved Asn of the heavy chain CH2 within the Fc region of antibodies is also important for maintaining mAb structure and stability and in some cases could regulate the downstream effector functions such as complement-dependent cytotoxicity (CDC) and antibody-dependent cellular cytotoxicity (ADCC) through modulating the binding to the $F_c\gamma$ receptors (Jennewein, M. F.; Alter, G. *Trends in Immunology.* 2017, 38, 358-372). Therefore, it is essential to characterize and control the levels of PTMs, particularly for those considered as CQAs during development, production and storage of therapeutic antibodies to ensure product quality and to define any potential effects on the ultimate safety and potency.

Peptide mapping with liquid chromatography-mass spectrometry (LC-MS) is used within the biopharmaceutical industry to characterize therapeutic antibodies at the molecular level (Beck et al., *Anal. Chem.* 2013, 85, 715-736; Sandra, K. et al., *J. Chromatogr. A.* 2014, 1335, 81-103). This method employs a bottom-up methodology, including enzymatic (i.e., typically trypsin) digestion of proteins under non-reducing (non-reduced peptide mapping) or reducing (reduced peptide mapping) conditions followed by separation of the resulting peptides and analysis via ultraviolet (UV) detection and/or mass spectrometry (MS), offering advantages of assessing the structural integrity maintained by inter- and intra-chain disulfide bonds, confirming the protein amino acid sequence, and providing site-specific quantitation upon post-translational and chemical modifications that may arise during production, processing or storage (Mouchahoir, T.; Schiel, J. E. *Anal. Bioanal. Chem.* 2018, 410, 2111-2126).

In the LC-MS based peptide mapping method for PTM analysis, a site-specific PTM is quantified from MS1 spectra of enzymatic digests by calculating the ratio of the extracted ion chromatogram (EIC) peak area of the modified peptide containing the PTM to the sum of the EIC peak areas of the corresponding native peptide and modified peptide. Although streamlined peptide mapping workflow can generate high sequence coverage and efficiently characterize multiple attributes (e.g., different site-specific PTMs) of an antibody sample in a single LC-MS run due to the rapid advancement of LC-MS instrumentation and bioinformatics software, this traditional label-free approach for relative quantitation of site-specific PTMs requires sample preparation and mass spectrometry data acquisition for individual samples, which can take substantial amounts of time, making it difficult to accommodate the ever-increasing demands for monoclonal antibody characterization during the drug development. Recent research advancement towards peptide mapping technology have been mainly focused on the improvement of sample preparation efficiency such as developing automation system to increase the throughput or on-line digestion system to reduce sample preparation time (Richardson et al., *Anal. Biochem.* 2011, 411, 284-291; Cao et al., *J. Pharm. Sci.* 2019, 108, 3540-3549; and Mao et al., *mAbs.* 2019, 11, 767-778), however when sample size increases instrument time required for LC-MS data acquisition of samples also increases linearly, which not only limits the overall efficiency of peptide mapping workflow for protein characterization, but also may bring in large variability to the PTM quantitation resulted from the time and temperature related instrument fluctuation, instrument hardware and software glitches or sample storage stability in the autosampler during the LC-MS analysis of digests in the peptide mapping.

BRIEF SUMMARY OF THE INVENTION

In one aspect, the present invention provides a method of quantifying multiple quality attributes of multiple samples in a single mass spectrometry (MS) run, comprising: contacting two or more samples with a digesting solution under conditions sufficient to digest the two or more samples, wherein each sample is digested separately and the digesting solution is a Tris-free buffer solution; contacting each of the two or more digested samples with a specific Tandem Mass Tag (TMT) labeling reagent under conditions sufficient to label peptides within each of the two or more digested samples with the specific TMT labeling reagent; quenching labeling of peptides within each of the two or more digested samples; combining equal volumes of the two or more labeled, digested samples into a single combined sample solution; and analyzing the single combined sample solution by targeted mass spectral analysis, thereby allowing multiple quality attributes of the two or more samples to be quantified in a single mass spectrometry (MS) run.

In some embodiments, multiple quality attributes comprise a post translational modification (PTM).

In some embodiments, the PTM comprises one or more of deamidation, oxidation, glycation, disulfide formation, N-terminal pyroglutamate formation, C-terminal lysine removal, and glycosylation.

In some embodiments, the PTM comprises glycosylation.

In some embodiments, quantifying multiple quality attributes in a single MS run, comprises quantifying PTMs by quantifying relative abundance of PTM from extracted peak areas of a resultant report ion generated in targeted mass spectra.

In some embodiments, the method further comprises contacting each of the two or more digested samples with a small molecule additive prior to contacting each of the two or more digested samples with a specific TMT labeling reagent.

In some embodiments, the small molecule additive is selected from the group consisting of BOC—Y—OH, p-Cresol, Hydroxy-phenyl acetic acid (HPAA), hydroxy benzoic acid (HBA), acetaminophen, and p-Amino Benzoic acid (PABA).

In some embodiments, the small molecule additive is PABA.

In some embodiments, the peptides are glycopeptides.

In some embodiments, the glycopeptides are obtained from a monoclonal antibody.

In some embodiments, the monoclonal antibody is of isotype IgG1, IgG2, IgG3, IgG4, or mixed isotype.

In some embodiments, two or more samples are between 2 and 16 samples.

In some embodiments, the method further comprises obtaining two or samples to be analyzed.

In some embodiments, the method further comprises preparing the two or more samples for digestion prior to contacting the two or more samples with a digesting solution under conditions sufficient to digest the two or more samples, In some embodiments, preparing the two or more samples prior to digestion comprises contacting each of the two or more samples with a denaturing and reducing solution under conditions that permit sample denaturation and reduction; and contacting each of the two or more denatured and reduced samples with an alkylating solution under conditions that permit sample alkylation.

In some embodiments, analyzing the single combined sample solution by targeted mass spectral analysis comprises applying the single combined sample to a separation column and performing targeted mass spectral analysis on eluted sample components.

In some embodiments, the separation column is a liquid chromatography column.

In some embodiments, performing targeted mass spectral analysis on eluted sample components comprises applying electrospray ionization to generate charged ions from the eluted sample components and measuring the generated charge ions.

In one aspect of the invention, a method of quantifying post translational modifications (PTMs) of multiple samples in a single mass spectrometry (MS) run, comprises contacting two or more samples with a digesting solution under conditions sufficient to digest the two or more samples, wherein each sample is digested separately and the digesting solution is a Tris-free buffer solution; contacting each of the two or more digested samples with a small molecule additive; contacting each of the two or more digested samples with a specific Tandem Mass Tag (TMT) labeling reagent under conditions sufficient to label peptides within each of the two or more digested samples with the specific TMT labeling reagent; quenching labeling of peptides within each of the two or more digested samples; combining equal volumes of the two or more labeled, digested samples into a single combined sample solution; and analyzing the single combined sample solution by targeted mass spectral analysis, thereby allowing PTMs of the two or more samples to be quantified in a single MS run.

In some embodiments, the PTM comprises one or more of deamidation, oxidation, glycation, disulfide formation, N-terminal pyroglutamate formation, C-terminal lysine removal, and glycosylation.

In some embodiments, the PTMs comprise glycosylation.

In some embodiments, quantifying PTMs comprises quantifying relative abundance of PTM from extracted peak areas of a resultant report ion generated in targeted mass spectra.

In some embodiments, the small molecule additive is selected from the group consisting of BOC—Y—OH, p-Cresol, Hydroxy-phenyl acetic acid (HPAA), hydroxy benzoic acid (HBA), acetaminophen, and p-Amino Benzoic acid (PABA).

In some embodiments, the small molecule additive is PABA.

In some embodiments, the peptides are glycopeptides.

In some embodiments, the glycopeptides are obtained from a monoclonal antibody.

In some embodiments, the monoclonal antibody is of isotype IgG1, IgG2, IgG3, IgG4, or mixed isotype.

In some embodiments, the two or more samples are between 2 and 16 samples.

In some embodiments, the method further comprises obtaining two or samples to be analyzed.

In some embodiments, the method further comprises preparing the two or more samples for digestion prior to contacting the two or more samples with a digesting solution under conditions sufficient to digest the two or more samples.

In some embodiments, preparing the two or more samples prior to digestion comprises contacting each of the two or more samples with a denaturing and reducing solution under conditions that permit sample denaturation and reduction; and contacting each of the two or more denatured and reduced samples with an alkylating solution under conditions that permit sample alkylation.

In some embodiments, analyzing the single combined sample solution by targeted mass spectral analysis comprises applying the single combined sample to a separation column and performing targeted mass spectral analysis on eluted sample components.

In some embodiments, the separation column is a liquid chromatography column.

In some embodiments, performing targeted mass spectral analysis on eluted sample components comprises applying electrospray ionization to generate charged ions from the eluted sample components and measuring the generated charge ions.

In various embodiments, any of the features or components of embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges and all values falling within such ranges are encompassed within the scope of the present disclosure. Each of the values discussed above or herein may be expressed with a variation of 1%, 5%, 10% or 20%. For example, a concentration of 10 mM may be expressed as 10 mM±0.1 mM (1% variation), 10 mM±0.5 mM (5% variation), 10 mM±1 mM (10% variation) or 10 mM±2 mM (20% variation). Other embodiments will become apparent from a review of the ensuing detailed description.

DESCRIPTION OF THE FIGURES

FIG. 7A depicts PTMs with levels>2.5% and FIG. 7B depicts PTMs with levels s 2.5%. Black error bars: standard deviation of PTM percentages in duplicate. The ordering of bars from left to right for each site-specific PTM for both FIGS. 7A and 7B is mAb-F-P1 (no TMT), mAb-F-P1 (TMT-128), mAb-F-P2 (no TMT), mAb-F-P2 (TMT-129), mAb-F-P3 (no TMT), mAb-F-P3 (TMT-130), mAb-F-P4 (no TMT), mAb-F-P4 (TMT-131).

FIG. 9 shows the effects of different small molecule additives during the TMT labeling on the relative abundances of TMT-labeled species with different TMT tags and different isoforms for WQQG peptide (residues 1-4 of SEQ ID NO: 3) and TTPP peptide (residues 1-4 of SEQ ID NO: 4). TMT labeling sites in each species were highlighted (bold). Boc-Y: N-(tert-Butoxycarbonyl)-tyrosine; HPAA: 4-hydroxyphenylacetic acid; HBA: 4-hydroxybenzoic acid; PABA: 4-aminobenzoic acid.

DETAILED DESCRIPTION OF THE INVENTION

Figure 1A:
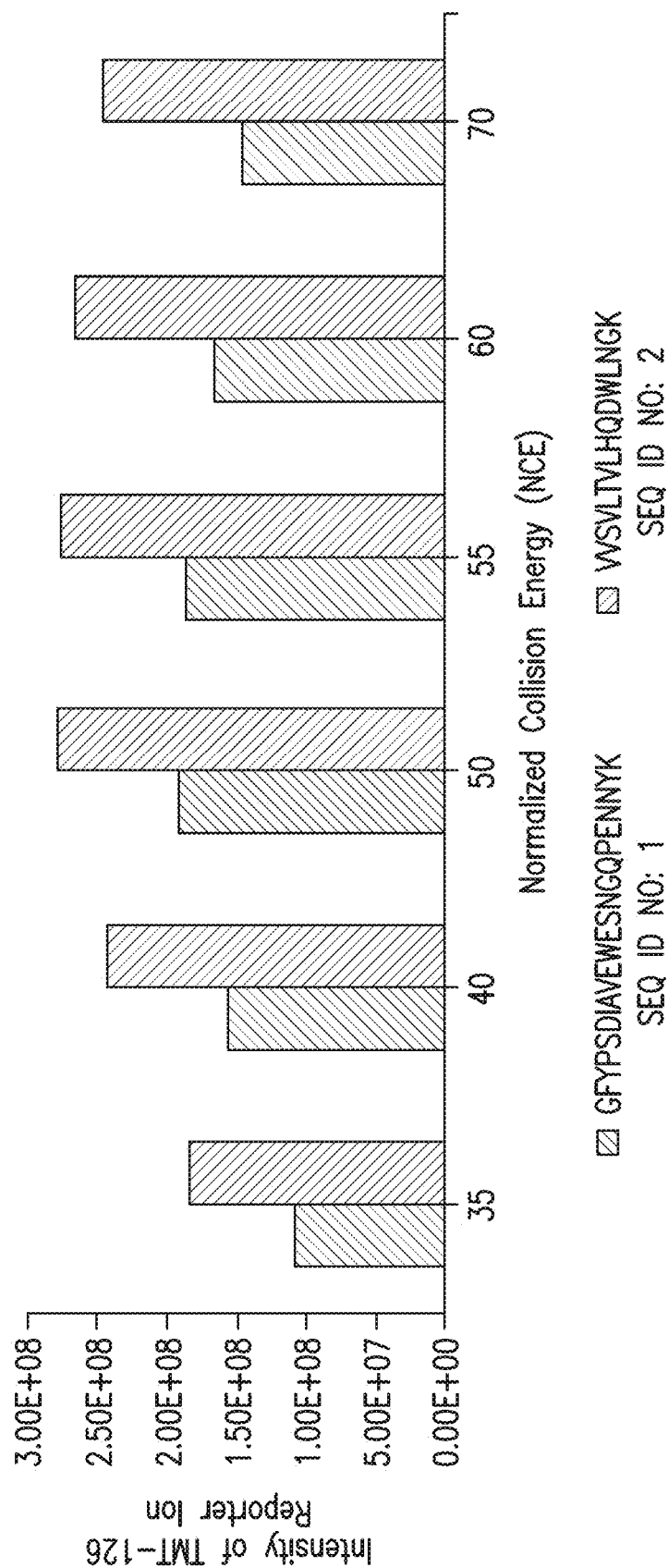
FIGS. 1A and 1B show the effects of NCE (35-70) on the report ion abundances of two representative TMT-labeled peptides in mAb-A (FIG. 1A) and on the relative quantitation of different types of PTMs in mAb-A along with PTM quantitative results from the conventional approach (FIG. 1B). For FIG. 1B, the ordering of columns from left to right for each site-specific PTM is control (no TMT), NCE 35, NCE 40, NCE 50, NCE 55, NCE 60, NCE 70.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims. Any embodiments or features of embodiments can be combined with one another, and such combinations are expressly encompassed within the scope of the present invention.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.)

Although any methods and materials similar or equivalent to those described herein can be used in the practice or testing of the present invention, the preferred methods and materials are now described. All patents, applications and non-patent publications mentioned in this specification are incorporated herein by reference in their entireties.

Abbreviations Used Herein

ACN: Acetonitrile
ADCC: antibody-dependent cellular cytotoxicity
Asn: Asparagine
AUC: Area Under Curve
Boc-Y: N-(tert-Butoxycarbonyl)-tyrosine
CDC: Complement-Dependent Cytotoxicity
CDR: Complementarity-Determining Region
CQA: Critical Quality Attributes
CV: Coefficient of Variations
EIC: Extracted Ion Chromatograph
ELISA: Enzyme-Linked Immunosorbent Assay
ESI-MS: Electrospray Ionization Mass Spectrometry
FA: Formic Acid
FDA: Food and Drug Administration
FLR: Fluorescent Detection
HBA: 4-hydroxybenzoic acid
HC: Heavy Chain
HILIC: Hydrophilic Interaction Liquid Chromatography
HPAA: 4-hydroxyphenylacetic acid
IgG: Immunoglobulin G
LC: Light Chain
LC-MS: Liquid Chromatography-Mass Spectrometry
mAb: Monoclonal Antibody
Met: Methionine
MS: Mass Spectrometry
MW: Molecular Weight
NCE: Normalized Collision Energy
PABA: 4-aminobenzoic acid
PK: Pharmacokinetics
PROCA: Procainamide
PQA: Product Quality Attribute
PTM: Post-translational Modification
RP-LC-MS/MS: Reversed Phase Liquid Chromatography Tandem Mass Spectrometry
SPE: Solid Phase Extraction
TCEP-HCl: Tris (2-carboxyethyl) Phosphine Hydrochloride
TFA: Trifluoroacetic Acid
TMT: Tandem Mass Tag
UV: Ultraviolet

Definitions

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). In various embodiments, the heavy chain may be an IgG isotype. In some cases, the heavy chain is selected from IgG1, IgG2, IgG3 or IgG4. In some embodiments, the heavy chain is of isotype IgG1 or IgG4, optionally including a chimeric hinge region of isotype IgG1/IgG2 or IgG4/IgG2. Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. For a review on antibody structure, see Lefranc et al., *IMGT unique numbering for immunoglobulin and T cell receptor variable domains and Ig superfamily V-like domains,* 27(1) Dev. Comp. Immunol. 55-77 (2003); and M. Potter, *Structural correlates of immunoglobulin diversity,* 2(1) Surv. Immunol. Res. 27-42 (1983).

The term antibody also encompasses "bispecific antibody", which includes a heterotetrameric immunoglobulin that can bind to more than one different epitope. One half of the bispecific antibody, which includes a single heavy chain and a single light chain and six CDRs, binds to one antigen or epitope, and the other half of the antibody binds to a different antigen or epitope. In some cases, the bispecific antibody can bind the same antigen, but at different epitopes or non-overlapping epitopes. In some cases, both halves of the bispecific antibody have identical light chains while retaining dual specificity. Bispecific antibodies are described generally in U.S. Patent App. Pub. No. 2010/0331527 (Dec. 30, 2010).

The term "antigen-binding portion" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et al. (1993) 90 PNAS U.S.A. 6444-6448; and Poljak et al. (1994) 2 Structure 1121-1123).

Moreover, antibodies and antigen-binding fragments thereof can be obtained using standard recombinant DNA techniques commonly known in the art (see Sambrook et al., 1989). Methods for generating human antibodies in transgenic mice are also known in the art. For example, using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to a desired antigen are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody The term "human antibody", is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

As used herein, the term "subject" refers to an animal, preferably a mammal, more preferably a human, for example in need of amelioration, prevention and/or treatment of a disease or disorder.

A "post-translational modification" (PTM) refers to the covalent modification of proteins following protein biosynthesis. Post-translational modifications can occur on the amino acid side chains or at the protein's C- or N-termini. Exemplary post-translational modifications of antibodies include deamidation, oxidation, glycation, disulfide formation, N-terminal pyroglutamate formation, C-terminal lysine removal, and glycosylation.

The term "tandem mass tag" (TMT) is a chemical label used for mass spectrometry (MS)-based quantification and identification of biological macromolecules such as proteins, peptides and nucleic acids. TMT belongs to a family of reagents referred to as isobaric mass tags. They provide an alternative to gel- or antibody-based quantification but may also be used in combination with these and other methods. In addition to aiding in protein quantification, TMT tags can also increase the detection sensitivity of certain highly hydrophilic analytes, such as phosphopeptides, in RPLC-MS analyses. There are currently six varieties of TMT available commercially (Thermo Fisher Scientific, Altham, MA, USA): TMTzero, a non-isotopically substituted core structure; TMTduplex, an isobaric pair of mass tags with a single isotopic substitution; TMTsixplex, an isobaric set of six mass tags with five isotopic substitutions; TMT 10-plex—a set of 10 isotopic mass tags which use the TMTsixplex reporter region, but use different elemental isotope to create a mass difference of 0.0063 Da, TMTpro a 16 plex version with a different reporter and mass normalizer than the original TMT, and TMTpro Zero. The tags contain four regions, namely a mass reporter region (M), a cleavable linker region (F), a mass normalization region (N) and a protein reactive group (R). The chemical structures of all the tags are identical but each contains isotopes substituted at various positions, such that the mass reporter and mass normalization regions have different molecular masses in each tag. The combined M-F-N-R regions of the tags have the same total molecular weights and structure so that during chromatographic or electrophoretic separation and in single MS mode, molecules labelled with different tags are indistinguishable. Upon fragmentation in MS/MS mode, sequence information is obtained from fragmentation of the peptide back bone and quantification data are simultaneously obtained from fragmentation of the tags, giving rise to mass reporter ions.

The term as used herein, "glycopeptide/glycoprotein" is a modified peptide/protein, during or after their synthesis, with covalently bonded carbohydrates or glycan. In certain embodiments, a glycopeptide is obtained from a monoclonal antibody, for example, from a protease digest of a monoclonal antibody.

The term as used herein, "glycan" is a compound comprising one or more of sugar units which commonly include glucose (Glc), galactose (Gal), mannose (Man), fucose (Fuc), N-acetylgalactosamine (GalNAc), N-acetylglucosamine (GlcNAc) and N-acetylneuraminic acid (NeuNAc) (Frank Kjeldsen, et al. Anal. Chem. 2003, 75, 2355-2361). The glycan moiety in glycoprotein, such as a monoclonal antibody, is an important character to identify its function or cellular location. For example, a specific monoclonal antibody is modified with specific glycan moiety.

The term "sample," as used herein, refers to a mixture of molecules that comprises at least an analyte molecule, e.g., glycopeptide, such as obtained from a monoclonal antibody, that is subjected to manipulation in accordance with the methods of the invention, including, for example, separating, analyzing, extracting, concentrating or profiling.

The terms "analysis" or "analyzing," as used herein, are used interchangeably and refer to any of the various methods of separating, detecting, isolating, purifying, solubilizing, detecting and/or characterizing molecules of interest (e.g., peptides). Examples include, but are not limited to, solid phase extraction, solid phase micro extraction, electrophoresis, mass spectrometry, e.g., ESI-MS, SPE HILIC, or MALDI-MS, liquid chromatography, e.g., high performance, e.g., reverse phase, normal phase, or size exclusion, ion-pair liquid chromatography, liquid-liquid extraction, e.g., accelerated fluid extraction, supercritical fluid extraction, microwave-assisted extraction, membrane extraction, soxhlet extraction, precipitation, clarification, electrochemical detection, staining, elemental analysis, Edmund degradation, nuclear magnetic resonance, infrared analysis, flow injection analysis, capillary electrochromatography, ultraviolet detection, and combinations thereof.

The term "profiling," as used herein, refers to any of various methods of analysis which are used in combination to provide the content, composition, or characteristic ratio of proteins, such as a peptide in a sample.

"Contacting," as used herein, includes bringing together at least two substances in solution or solid phase.

"Targeted mass spectrometry," as used herein, is a mass spectrometry technique that uses multiple stages of tandem mass spectrometry (MSn with n=2 or 3) for ions of specific mass (m/z), at specific time. The values of the m/z and time are defined in an inclusion list which is derived from a previous analysis.

"Tandem mass spectrometry," also known as MS/MS or MS2, is a technique in instrumental analysis where two or more mass spectrometers are coupled together using an additional reaction step to increase their abilities to analyze chemical samples. A common use of tandem-MS is the analysis of biomolecules, such as proteins and peptides. The molecules of a given sample are ionized and the first spectrometer (designated MS1) separates these ions by their mass-to-charge ratio (often given as m/z or m/Q). Ions of a particular m/z-ratio coming from MS1 are selected and then made to split into smaller fragment ions, e.g. by collision-induced dissociation, ion-molecule reaction, or photodissociation. These fragments are then introduced into the second mass spectrometer (MS2), which in turn separates the fragments by their m/z-ratio and detects them. The fragmentation step makes it possible to identify and separate ions that have very similar m/z-ratios in regular mass spectrometers.

General Description

Peptide mapping coupled with liquid chromatography-mass spectrometry (LC-MS) has become a key analytical technique to quantify the quality attributes (e.g., post-translational modifications (PTMs)) of monoclonal antibodies during the drug development. However, the traditional label-free approach for the relative quantitation of PTMs requires a great amount of the instrument time for LC-MS data acquisition of individual digested samples, which limits the efficiency of peptide mapping technique especially with an ever-increasing demand for protein characterization.

Thus, there is a need for protein characterization methods with increased efficiency. The disclosed invention meets that need.

Disclosed herein is a new tandem mass tag (TMT) based approach in combination with targeted mass spectrometry for multiplexed site-specific PTM quantitation of proteins, including monoclonal antibodies. This new method is based upon studies reported herein wherein the inventors made the surprising discovery that this approach enables the simultaneous quantitation of quality attributes (e.g., PTMs) for multiple samples in a single LC-MS run. In particular, with this method, multiple digested antibody samples are chemically labeled with tandem mass tag variants, combined with equal volume and then analyzed using targeted mass spectrometry. Differentially labeled peptides are indistinguishable in the full MS spectrum of intact peptides because of the same molecular structure and mass of each variant, but each variant labeled peptide produces a unique "report ion" in the MS/MS spectrum when fragmented inside a mass spectrometer, therefore distinguishing the peptide in different samples and representing the abundance of peptide in the corresponding sample. The relative abundance of PTM in each sample is quantified from extracted peak areas of the resultant report ion generated from corresponding variant labeled native and modified peptides in the targeted MS/MS spectra thereby allowing the simultaneous quantitation of multiple quality attributes (e.g., PTMs) for multiple samples, such as up to 16-plex due to current multiplexing capacity of commercial TMT reagent, in a single LC-MS run, resulting in the significantly reduced data acquisition time and run-to-run variation in the PTM quantitation.

In some embodiments, the method includes preparing TMT peptides. In some embodiments, sample preparation includes contacting a sample with a denaturing and reducing solution under conditions that permit sample denaturation and reduction; contacting denatured and reduced sample with an alkylating solution under conditions that permit sample alkylation; contacting alkylated sample with a digest solution under conditions that permit sample digestion and TMT labeling; and contacting digested sample with a quenching solution under conditions that stop sample digestion. The prepared TMT peptides can then be analyzed, such as by LC-MS.

Figure 10:
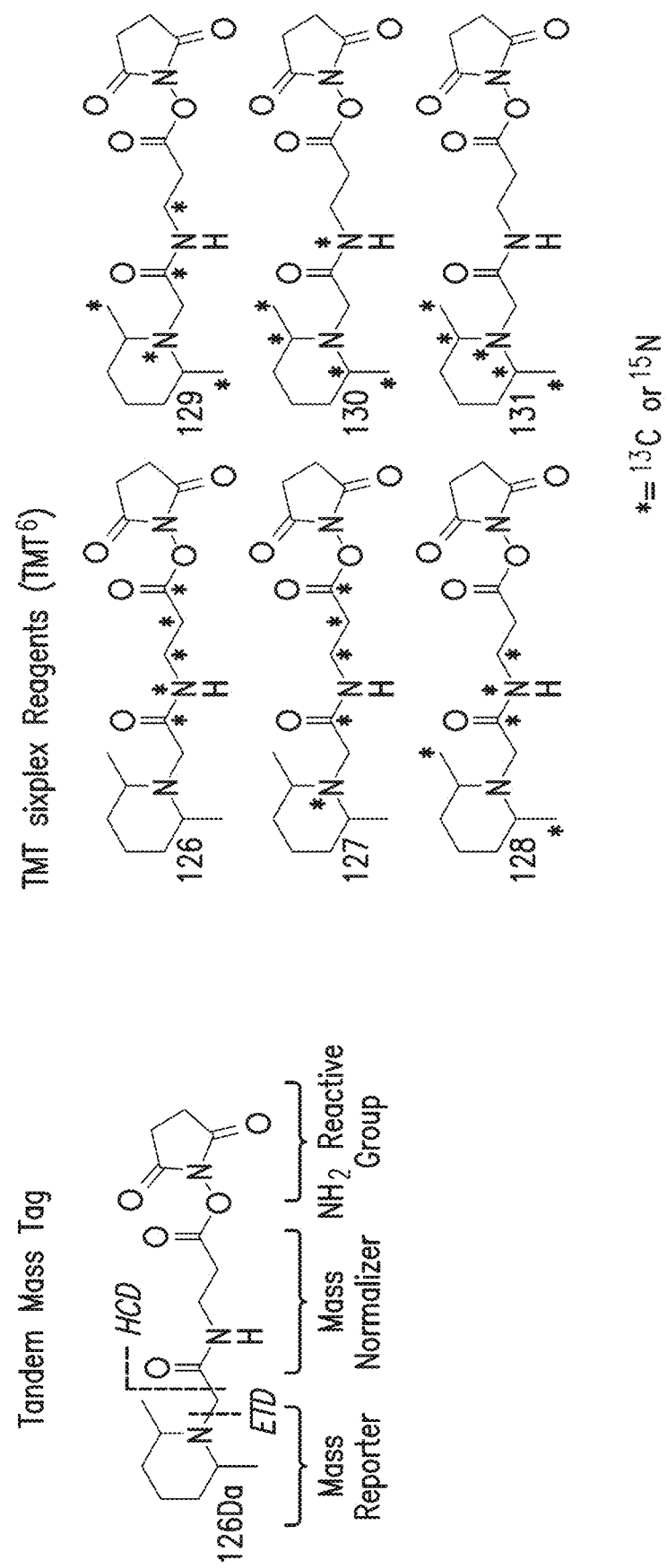
FIG. 10 shows structure of an exemplary tandem mass tag and exemplary tandem mass tag reagents.
Figure 11:
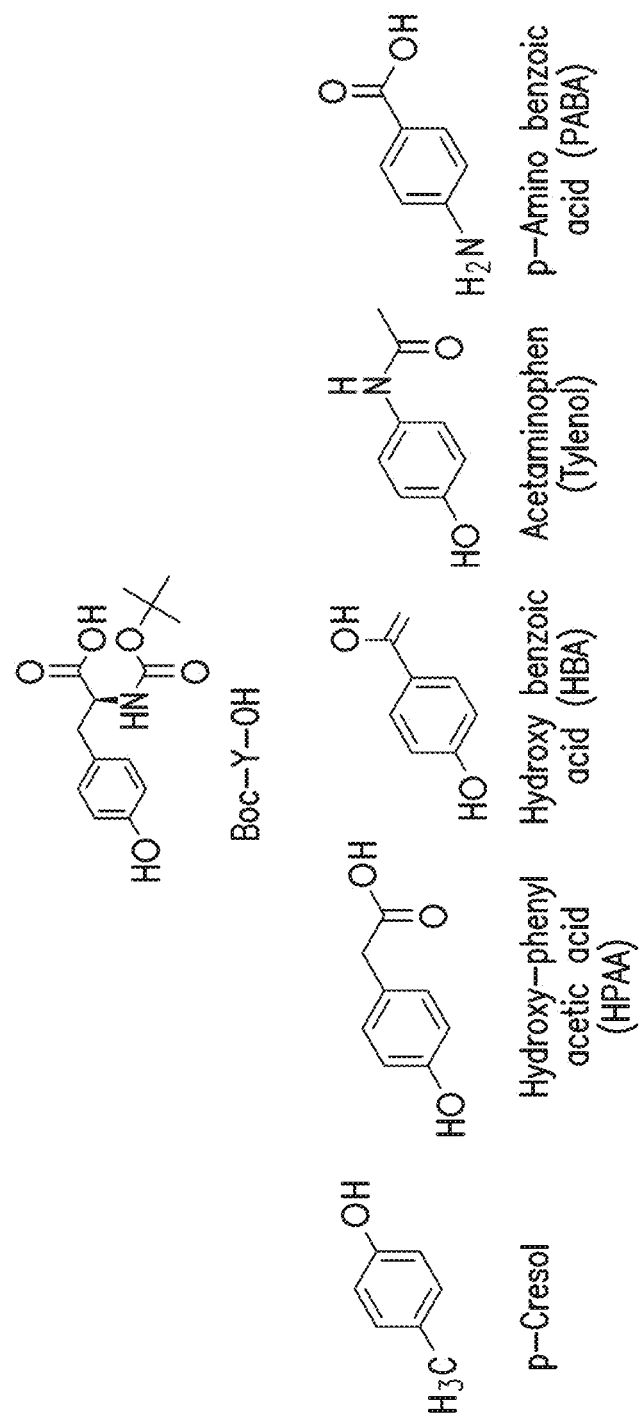
FIG. 11 shows the chemical structures of exemplary over-labeling preventing reagents —BOC—Y—OH, p-Cresol, Hydroxy-phenyl acetic acid (HPAA), hydroxy benzoic acid (HBA), acetaminophen, and/or p-Amino Benzoic acid (PABA).

In some embodiments, contacting the sample with a digest solution under conditions that permit digestion includes following a standard digesting protocol except in a Tris-free buffer, such as in a phosphate buffered saline (PBS) solution, pH 7.5 to 8. In some embodiments, the pH of the PBS solution is adjusted prior to adding a TMT reagent to the digesting solution. Tandem Mass Tag (TMT) sets are reagents which react easily with peptides (N-terminus and lysine, any basic $NH_2$); have equivalent molecular weight (same MS1 mass); and generate different MS2 reporter fragment ions due to heavy-atom distribution around each tag. Exemplary TMTs are provided in FIG. 10 and are commercially available from Thermo Fisher Scientific (Waltham, MA, USA). Although commercially available TMTs are known to only react with $NH_2$ groups (N-terminus, Lysine), the inventors discovered herein that TMTs can also react significantly with OH groups (Tyrosine, Threonine, Serine). This reactivity was problematic in that it complicated integrations, splitting up each peptide into multiple forms, reducing the signal of each peak and resulting in over-labeling of TMT. The method disclosed herein solves these limitations by adding a high concentration of a small molecule additive (e.g., 100 mol small molecule additive/mol of peptide) that allows a TMT to still react quickly with $NH_2$— groups on the peptides, but redirects excess TMT away from the peptides allowing the majority of TMT-peptide to exist in a single form and being easier to integrate. In some examples, this small molecule additive is BOC—Y—OH, p-Cresol, Hydroxy-phenyl acetic acid (HPAA), hydroxy benzoic acid (HBA), acetaminophen, and/or p-Amino Benzoic acid (PABA). The chemical structures of these reagents are provided in FIG. 11. In some embodiments, the method includes adding a small molecule additive to the digest sample prior to adding each TMT reagent. Each TMT reagent, such as commercially available TMT reagents from Thermo Fisher Scientific, is dissolved in ACN and added to each protein sample and allowed to incubate, such as at room temperature for 1 hour. All reactions are quenched, such as quenched to a pH less than 4 prior to being combined into one sample and subsequently evaluated LC-MS. In embodiments, the method includes preparing the sample for LC injection and evaluating it by running targeted MS2.

The disclosed method can be used with reduced (PTM %) and non-reduced (trisulfide %) peptide mapping. In embodiments, for non-reduced peptide mapping an over-labeling inhibitor, such as PABA, is not needed because the non-reduced peptides do not over-label.

In some embodiments, the sample comprises peptides. For example, the sample includes peptides with PTMs. In some embodiments, the peptides are glycopeptides, such as glycopeptides obtained from a monoclonal antibody. In some embodiments, the monoclonal antibody is of isotype IgG1, IgG2, IgG3, IgG4, or mixed isotype.

In some embodiments, the sample is a monoclonal antibody and the digest solution comprises one or more proteases, such as trypsin. In some examples, the method is used for characterizing/analyzing glycopeptides, such as glycopeptides obtained from a monoclonal antibody, such as an antibody that has been digested with one or more proteases. For example, the methods can be used to characterize the glycosylation of proteins, e.g., monoclonal antibody (mAb) therapeutics. In certain embodiments, the samples at any intervening step may be concentrated, diluted, desalted or the like.

In embodiments, the separation column is a liquid chromatography (LC) separation column. Liquid chromatography, including HPLC, can be used to analyze peptides, including monoclonal antibodies. Various forms of liquid chromatography can be used to study these structures, including anion-exchange chromatography, reversed-phase HPLC, size-exclusion chromatography, high-performance anion-exchange chromatography, and normal phase (NP) chromatography, including NP-HPLC (see, e.g., Alpert et al., *J. Chromatogr. A* 676:191-202 (1994)). Hydrophilic interaction chromatography (HILIC) is a variant of NP-HPLC that can be performed with partially aqueous mobile phases, permitting normal-phase separation of peptides, carbohydrates, nucleic acids, and many proteins. The elution order for HILIC is least polar to most polar, the opposite of that in reversed-phase HPLC. HPLC can be performed, e.g., on an HPLC system from Waters (e.g., Waters 2695 Alliance HPLC system), Agilent, Perkin Elmer, Gilson, etc.

In some embodiments, LC-MS/MS analysis is performed by using an ACQUITY UPLC peptide BEH C18 column. The column temperature can be maintained at a constant temperature throughout the chromatography run, e.g., using a commercial column heater. In some embodiments, the column is maintained at a temperature between about 18° C. to about 70° C., e.g., about 30° C. to about 60° C., about 40° C. to about 50° C., e.g., at about 20° C., about 25° C., about 30° C., about 35° C., about 40° C., about 45° C., about 50° C., about 55° C., about 60° C., about 65° C., or about 70° C. In some embodiments, the column temperature is about 40° C. In some embodiments, the run time can be between about 15 to about 240 minutes, e.g., about 20 to about 70 min, about 30 to about 60 min, about 40 to about 90 min, about 50 min to about 100 min, about 60 to about 120 min, about 50 to about 80 min. Following LC, the eluent is then subjected to MS/MS analysis.

In some embodiments, such as for targeted or untargeted LC-MS/MS analysis, the aliquot of each TMT-labeled sample is separated on an ACQUITY UPLC peptide BEH C18 column. The eluent is then electro-sprayed and analyzed by a Q-Exactive Plus hybrid mass spectrometer with HCD employed for peptide fragmentation for MS/MS experiments. A target list containing trigger m/z, z, targeted retention time window and collision energy of TMT-labeled native and modified peptides is loaded into the inclusion list to guide MS/MS analysis of precursors detected in MS1 survey scans. Peptide and PTM identification are then determined. In some embodiments, the percentage of each PTM is calculated using the extracted ion chromatogram (EIC) peak area of the modified peptide relative to the sum of the peak areas of the modified and native peptides.

EXAMPLES

The following examples are put forth so as to provide those of ordinary skill in the art with a complete disclosure and description of how to make and use the methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Materials and Chemicals

All human IgG1 and IgG4 monoclonal antibodies (mAb-A, mAb-B, mAb-C, mAb-D and mAb-E) in this study were produced at Regeneron (Tarrytown, NY). mAb-A stability samples were generated by incubating the control sample under different stressed conditions and labeled as mAb-A-S0 (Control), mAb-A-S1 (T=45° C., t=28 days), mAb-A-S2 (T=25° C., t=6 months) and mAb-A-S3 (T=5° C., t=24 months), respectively. mAb-B comparability samples were manufactured at four different process areas and labeled as mAb-B-P1, mAb-B-P2, mAb-B-P3 and mAb-B-P4, respectively. mAb-E trisulfide standards with different trisulfide levels were generated by mixing $H_2S$ stressed sample and reference standard sample at different ratios and labeled as mAb-E-TS0 (100:0), mAb-E-TS1 (75:25), mAb-E-TS2 (50:50), mAb-E-TS3 (25:75) and mAb-E-TS4 (0:100), respectively. Rapid Peptide N-glycosidase F (Rapid PNGase F) with 5×Rapid PNGase F buffer was purchased from New England Biolabs Inc. (lpswich, MA). Glacial acetic acid (Purity 99%), iodoacetamide, sodium phosphate monobasic, sodium phosphate dibasic, 4-aminobenzoic acid (PABA), 4-hydroxybenzoic acid (HBA), 4-hydroxyphenylacetic acid (HPAA) and N-(tert-Butoxycarbonyl)-tyrosine (Boc-Y) were purchased from Sigma (St. Louis, MO, USA). Sequencing grade trypsin and Asp-N were purchased from Promega (Madison, WI). Tandem Mass Tag (TMT) isobaric reagents, tris (2-carboxyethyl) phosphine hydrochloride (TCEP-HCl), trifluoroacetic acid (TFA, sequencing grade) and acetonitrile (Optima LC/MS) were purchased from Thermo Fisher Scientific (Waltham, MA). UltraPure 1.0 M Tris-HCl (pH 7.5) was purchased from Invitrogen Life Technologies (Carlsbad, CA), and high purity water was purchased from Milli-Q system (Bedford, MA).

Reduced Peptide Mapping of mAbs. Reduced peptide mapping was performed to quantify the PTM levels (e.g., N-terminal Gln/Glu cyclization, Met oxidation, Asn deamidation, Asp cyclization/isomerization, C-terminal Lys clipping, Lys glycation, and Fc glycosylation) for mAb-A stability and mAb-B comparability samples. A 500 μg of each sample was buffer-exchanged into 5 mM acetic acid to remove TMT-reactive compounds (e.g., histidine, Tris-HCl), and then denatured and reduced in 5 mM acetic acid in the presence of 5 mM TCEP-HCl at 80° C. for 10 minutes. After denaturation and reduction, each sample was diluted with 100 mM PBS (pH 8.0) containing 8 M urea and alkylated with iodoacetamide for 30 minutes in the dark at room temperature. Following alkylation, each sample was further diluted with 50 mM PBS (pH 8.0) to reduce the urea concentration to less than 1 M. For trypsin digestion, each diluted sample was incubated with trypsin at an enzyme to substrate ratio of 1:20 (w/w) at 37° C. for 4 hours. For Asp-N digestion, each diluted sample was incubated with Asp-N at an enzyme to substrate ratio of 1:50 (w/w) at 37° C. for 4 hours. To generate the deglycosylated sample for glycosylation quantitation, an aliquot of each trypsin digested sample was further incubated with PNGase F (1 mU/μg protein) for 1 more hour at 37° C. to remove N-linked glycans at peptide level. After trypsin, Asp-N or PNGase F digestion, each digested sample was divided into two equal aliquots. One aliquot was quenched by addition of 10% TFA to stop trypsin digestion and subjected to online LC-MS analysis, and the other aliquot was remained to the subsequent TMT labeling procedure.

Tryptic Peptide Mapping of Non-reduced mAbs. Non-reduced peptide mapping was performed to quantify the trisulfide levels for mAb-C, mAb-D and mAb-E trisulfide standards. A 500 μg of each sample was buffer-exchange into 100 mM PBS (pH 7.5) to remove TMT-reactive compounds (e.g., histidine, Tris-HCl), and then denatured in 8 M urea containing 1.0 mM iodoacetamide in 100 mM PBS, pH 7.5 at 50° C. for 10 minutes in the dark. After denaturation, 100 mM PBS (pH 7.5) was added to dilute the urea concentration 5-fold. Each sample was then digested with trypsin at an enzyme to substrate ratio of 1:20 (w/w) at 37° C. for 4 hours. After trypsin digestion, each digested sample was divided into two equal aliquots. One aliquot was quenched by addition of 10% TFA to stop trypsin digestion and subjected to online LC-MS analysis, and the other aliquot was remained to the subsequent TMT labeling procedure.

TMT Labeling of Reduced and Non-reduced mAb Digests. The TMT6-plex reagents were dissolved in 41 μL acetonitrile according to the manufacturer's protocol (Thermo Scientific). The aliquot of each digested sample (100 μg) in the reduced and non-reduced peptide mapping experiments incubated with 41 μL of a TMT tag dissolved in acetonitrile in the presence of over-labeling controlling reagent (PABA, HBA, HPAA or Boc-Y) (100 mol reagent/mol of protein) for 1 hour at ambient temperature for labeling. The labeling reaction was stopped by adding 10% TFA. TMT-labeled digests of mAb-A stability samples, mAb-B comparability samples and mAb-E trisulfide standards were pooled in equal amounts, respectively, and then subjected to LC-MS/MS analysis.

LC-MS/MS Analysis. For untargeted LC-MS/MS analysis, the aliquot (approximately 8 μg) of each digest was injected onto an ACQUITY UPLC peptide BEH C18 column (Waters, 2.1 mm×150 mm, 1.7 μm particle size, 130 Å pore size). Peptides were eluted with a linear gradient that was increased from 0.1% mobile phase B to 35% mobile phase B over 75 mins (mobile phase A: 0.05% TFA in water; mobile phase B: 0.045% TFA in acetonitrile) at a flow rate of 0.25 mL/min with column temperature of 40° C. The eluent was then electro-sprayed and analyzed by a Q-Exactive Plus hybrid mass spectrometer with higher-energy collision dissociation (HCD) employed for peptide fragmentation for MS/MS experiments. The instrument was operated in positive mode and set to the following acquisition parameters: MS1 resolution=70,000; MS1 AGC target=1×10$^6$; MS1 maximum inject time=50 ms; MS1 scan range=400-2,000 m/z; MS2 resolution=17,500; MS2 AGC target=1× 10$^5$; maximum inject time=100 ms; TopN=5; isolation window=4.0 m/z; normalized collision energy=27; underfill ratio=10%; peptide match=preferred; exclude isotopes=on; dynamic exclusion=10 s.

For targeted LC-MS/MS analysis, the aliquot of each TMT-labeled sample (approximately 8 μg) was separated on an ACQUITY UPLC peptide BEH C18 column (Waters, 2.1 mm×150 mm, 1.7 μm particle size, 130 Å pore size) with a longer linear gradient that was increased from 0.1% mobile phase B to 40% mobile phase B over 150 mins (mobile phase A: 0.05% TFA in water; mobile phase B: 0.045% TFA in acetonitrile) at a flow rate of 0.25 mL/min with column temperature of 40° C. The eluent was then electro-sprayed and analyzed by a Q-Exactive Plus hybrid mass spectrometer with HCD employed for peptide fragmentation for MS/MS experiments. A target list containing trigger m/z, z, targeted retention time window and collision energy of TMT-labeled native and modified peptides was loaded into the inclusion list to guide MS/MS analysis of precursors detected in MS1 survey scans. The instrument was operated in positive mode and set to the following acquisition parameters: MS1 resolution=17,500; MS1 AGC target=1×10$^6$; MS1 maximum inject time=50 ms; MS1 scan range=400-2,000 m/z; MS2 resolution=17,500; MS2 AGC target=1× 10$^5$; maximum inject time=100 ms; Fixed first mass=100; isolation window=2.0 m/z; normalized collision energy=27-100.

Data Analysis. Peptide and PTM identification were determined by Byonic (Protein Metrics Inc., San Carlos, CA; see Bern et al., *Curr. Protoc. Bioinformatics*. 2012, 40, 13.30.1-12.20.14) and verified manually. In the label-free approach for relative quantitation of site-specific PTMs, the extracted ion chromatograms in MS1 spectra, based on the m/z of the first isotope peak of both the native peptide and modified peptide, were generated and the extracted peak areas were integrated using skyline-daily (MacCoss Lab, University of Washington, WA; see MacLean et al., *Bioinformatics*. 2010, 26, 966-968).

The percentage of each PTM was calculated using the extracted ion chromatogram (EIC) peak area of the modified peptide relative to the sum of the peak areas of the modified and native peptides. In the targeted MS/MS based approach for relative quantitation of site-specific PTMs, the extracted ion chromatograms in MS/MS spectra, based on the m/z of the report ion of both the native peptide and modified peptide, were generated and the extracted peak areas were integrated using skyline-daily (MacCoss Lab, University of Washington, WA). The percentage of each PTM was calculated using the EIC peak area of the report ion from the modified peptide relative to the sum of the peak areas of the report ion from the modified and native peptides.

Example 2: HCD Collision Energy Optimization for PTM Quantitation

TMT peptides are labeled with isobaric amine reactive labels which generate quantitative information upon collisional activation. TMT report ions are formed through cleavage of the amide bond by collision energy to create a cluster of ions between 126 and 131 m/z in the low mass region of tandem mass spectra (Thompson et al., *Anal. Chem.* 2003, 75, 1895-1904). In the TMT-based approach for PTM quantitation, report ion generated in the targeted MS/MS spectra of the native peptide and modified peptide is employed for PTM percentage calculation. The abundance of TMT report ion generated in MS/MS spectra is correlated to the normalized collision energy (NCE) in the HCD cell applied to the TMT-labeled peptide. The effect of NCE (35-70) on the report ion abundances of TMT-labeled peptides in mAb-A was investigated as shown in FIG. 1A. The report ion intensities were maximized when NCE was increased up to 50 or 55, and then decreased by further increasing NCE to 70. However, the NCE of 35 tends to produce the abundant fragmentation information for peptide identification and greater NCE yields less fragmentation information as the increase of NCE. For instance, when NCE was increased to 70, only few fragmentation information was retained in the MS/MS spectra.

Figure 1B:
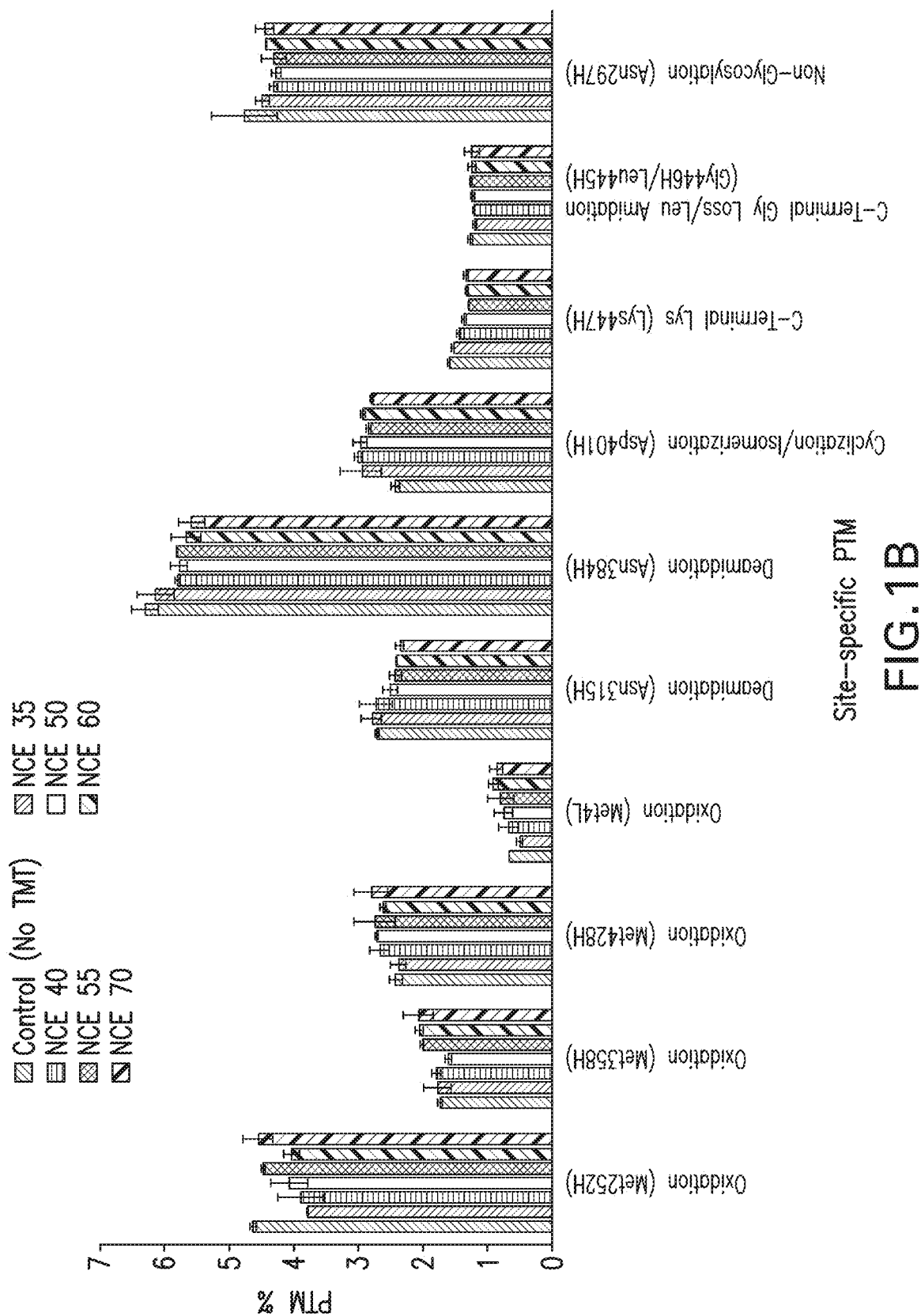

The quantitation of different PTM types in mAb-A by the report ion generated in the targeted MS/MS spectra of the native and modified peptides at different NCEs was examined for Met oxidation, Asn deamidation, Asp cyclization/isomerization, C-terminal Lys clipping and Fc glycosylation, and compared with PTM quantitation by conventional MS1-based approach. It is noted that there is no significant difference in the percentages of different PTMs at NCEs of 35-70, and PTM percentages were comparable to those quantified by using the conventional approach where the first isotope peak of the native and modified precursor peptides in the MS1 survey scans were used for percentage calculation (see FIG. 1B), which demonstrates the feasibility of targeted MS/MS based approach for PTM quantitation. The results also indicate that the changing tendency of the report ion abundance at different NCEs is similar between the native and modified peptides. To maximize the sensitivity of quantifying low abundant PTMs while maintaining the decent fragmentation information for peptide sequence confirmation, thus NCE 55 was selected for quantitation of Met oxidation, Asn deamidation, Asp cyclization/isomerization, C-terminal Lys clipping and Fc glycosylation.

Figure 2A:
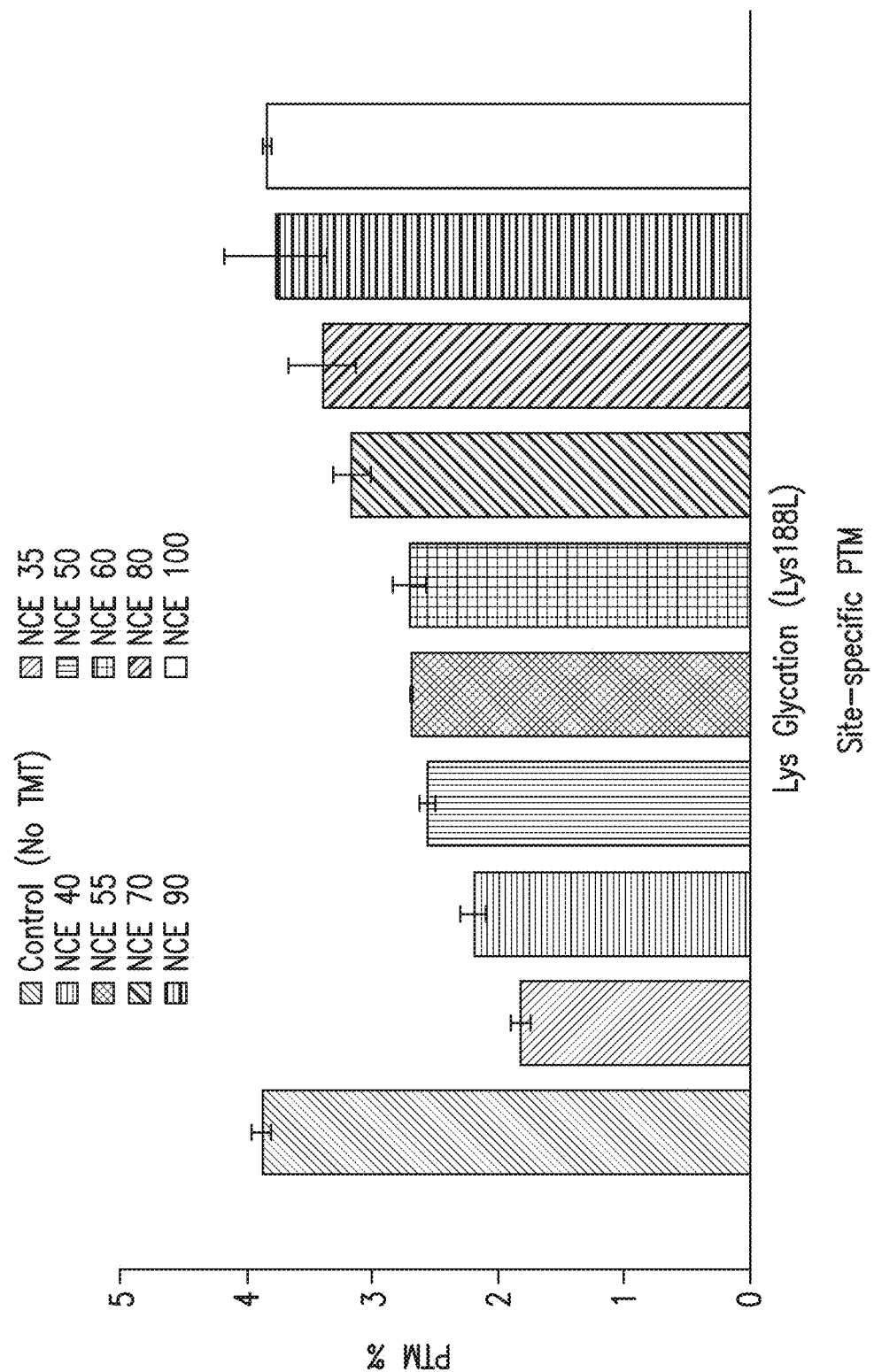
FIGS. 2A and 2B show the effects of NCE (35-100) on the quantitation of Lys glycation in mAb-B (FIG. 2A) and the effects of NCE (27-100) on the quantitation of pyroglutamate at N-terminal Glu in mAb-B (FIG. 2B). Black error bars: standard deviation of PTM percentages in duplicate. The ordering of columns for FIG. 2A (from left to right) is control (no TMT), NCE 35, NCE 40, NCE 50, NCE 55, NCE 60, NCE 70, NCE 80, NCE 90, and NCE 100. The ordering of columns for FIG. 2B (left to right) is control (no TMT), NCE 27, NCE 30, NCE 35, NCE 40, NCE 50, NCE 55, NCE 60, NCE 70, NCE 80, NCE 90, and NCE 100.
Figure 2B:
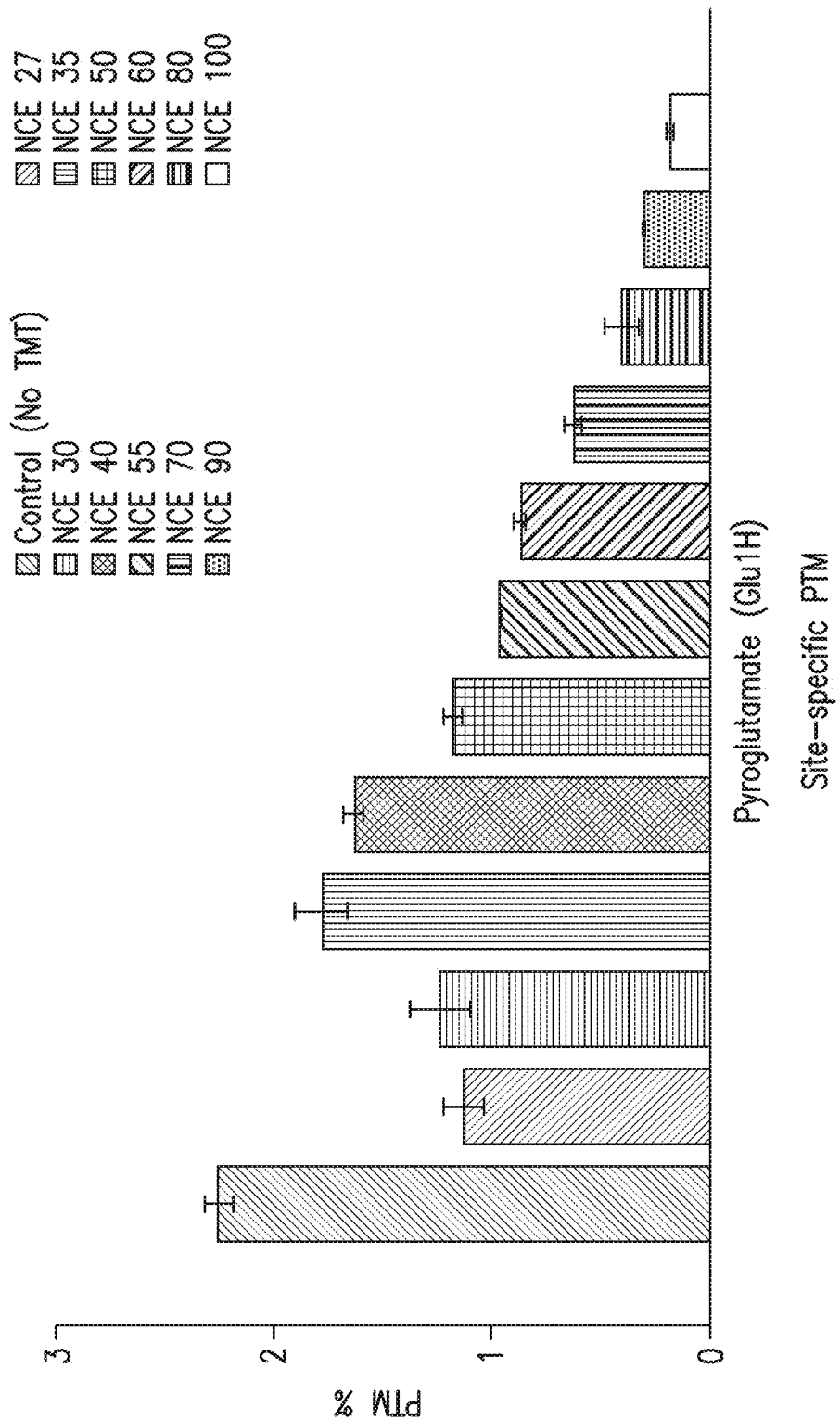

Cyclization of the N-terminal Gln or Glu at the light chain or heavy chain to form pyroglutamate (PyroE or PyroQ) is the major type of N-terminal modification (Liu et al., *mAbs*. 2014, 6, 1145-1154). However, this modification inhibits the reaction of the TMT labeling reagent with N-terminal amine group by blocking the N-terminus of the peptide, which restricts the capability of this multiplexing approach to quantify this modification. To overcome this limitation, the N-terminal peptides from mAb-A containing Gln or Glu at the N-terminus were examined but also a lysine residue at the C-terminus. In the native peptide both the N-terminal amine group and the ε-amino group of lysine side chain can be labeled with TMT tags, however in the modified peptide only the ε-amino group of lysine side chain can be labeled because of the blocked N-terminal amine group. To evaluate the feasibility of using the report ion generated from the native and modified peptides for this PTM quantitation, the percentages of pyroglutamate at different NCEs (27-100) were calculated and compared with that obtained from the conventional approach. As shown in FIG. 2B, this approach provided the most comparable result at NCE 35 relative to the conventional approach (NCE 35 also for PyroQ). The decreased percentage was observed at higher and lower NCE and with NCE 27 and NCE 55 the percentage of pyroglutamate was only ~50% of that from the conventional approach. Therefore, NCE 35 was selected for pyroglutamate quantitation.

The quantitation of Lys glycation in mAb-B and mAb-C (with different levels) by using the report ion was also investigated. Glycation is a non-enzymatic process that can result in the modification of primary amines by reducing sugars (e.g., glucose, fructose). Lysine residues are particularly susceptible to glycation within a protein with an increase of the side chain mass by 162.05 Da and generate charge heterogeneity by changing the primary amine side chain from basic to neutral (Liu et al., *mAbs*. 2014, 6, 1145-1154).

Because glycation of Lys inhibits the cleavage of the peptide bond by trypsin at the glycated Lys sites, resulting in a peptide with glycated Lys residues having different lengths compared to the peptide possessing native Lys residues. Therefore, to analyze the glycation products at the Lys site, peptide mapping with Asp-N digestion was performed. Similar to the N-terminal Gln/Glu pyroglutamate, glycation can change the physical property of the lysine residue, making the lysine residue not reactive to the TMT reagent and therefore different numbers of TMT tag labeled on the native peptide and glycated peptide. The investigation of the effect of different NCEs (35-100) on quantitation of this PTM revealed that different percentages were also obtained at different NCEs with higher NCE producing higher percentage of glycation. The comparable percentage relative to that quantified from the conventional approach can be achieved when NCE was increased up to 90-100 (FIG. 2). The observed strong dependence on NCE for PTM quantitation of pyroglutamate and glycation may be due to the incoherent change tendencies of the report ion abundance with different NCEs between the native peptide and modified peptide. For example, the report ion abundance was maximized at different NCEs of 55 and 70 for native peptide and glycated peptide, respectively. To achieve the comparable quantitation to the conventional approach, NCE 90 was thus selected to quantify the Lys glycation. It should be noted that due to the lack of the rich fragmentation information, a pre-run with a lower NCE (such as 35) can be used to confirm the peptide sequence and lysine modification.

Figure 3A:
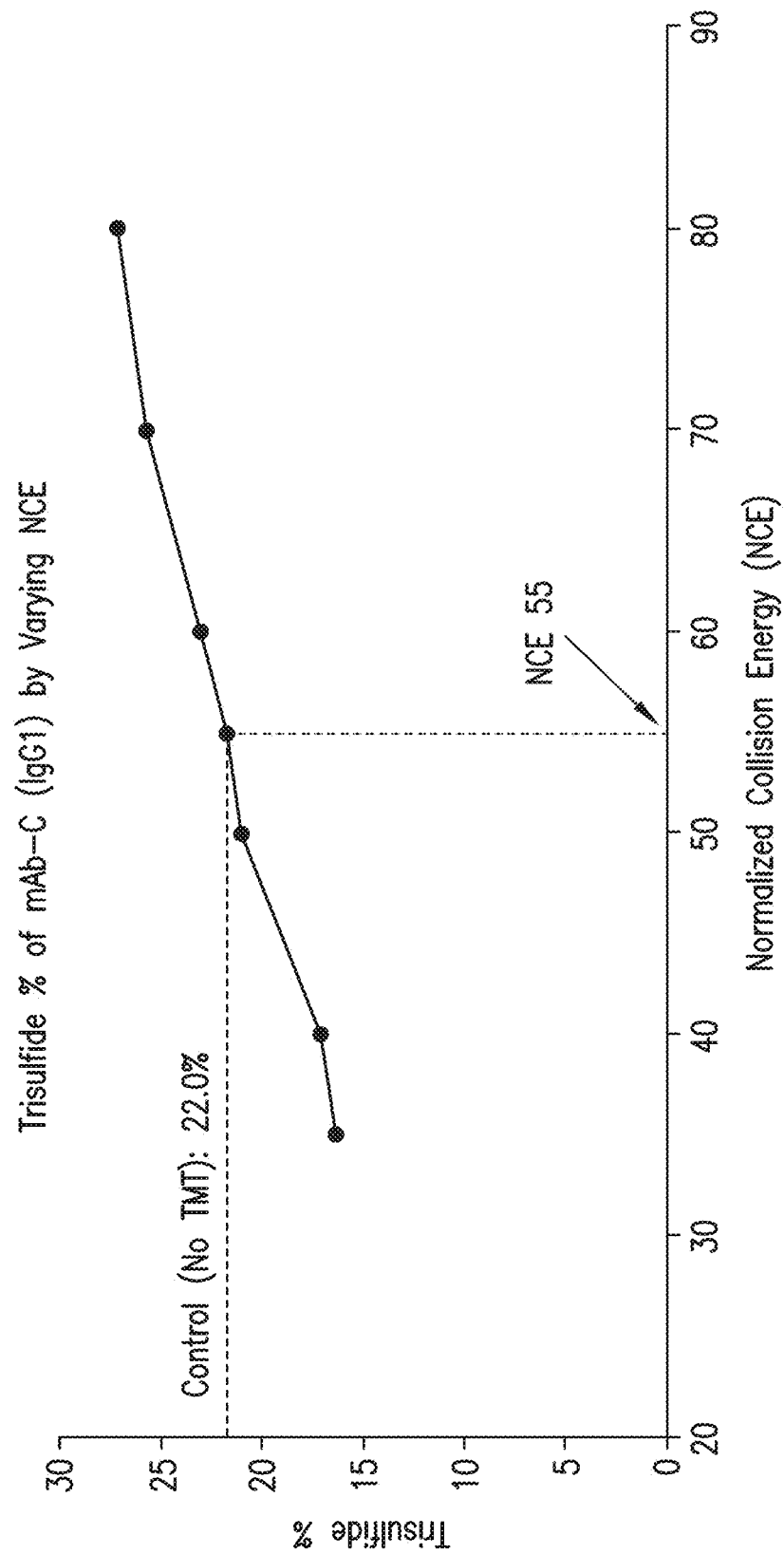
FIGS. 3A and 3B show the effects of NCE (35-80) on the trisulfide quantitation in IgG1 mAb-C (FIG. 3A) and IgG4 mAb-D (FIG. 3B) along with the quantitative results from the conventional approach.
Figure 3B:
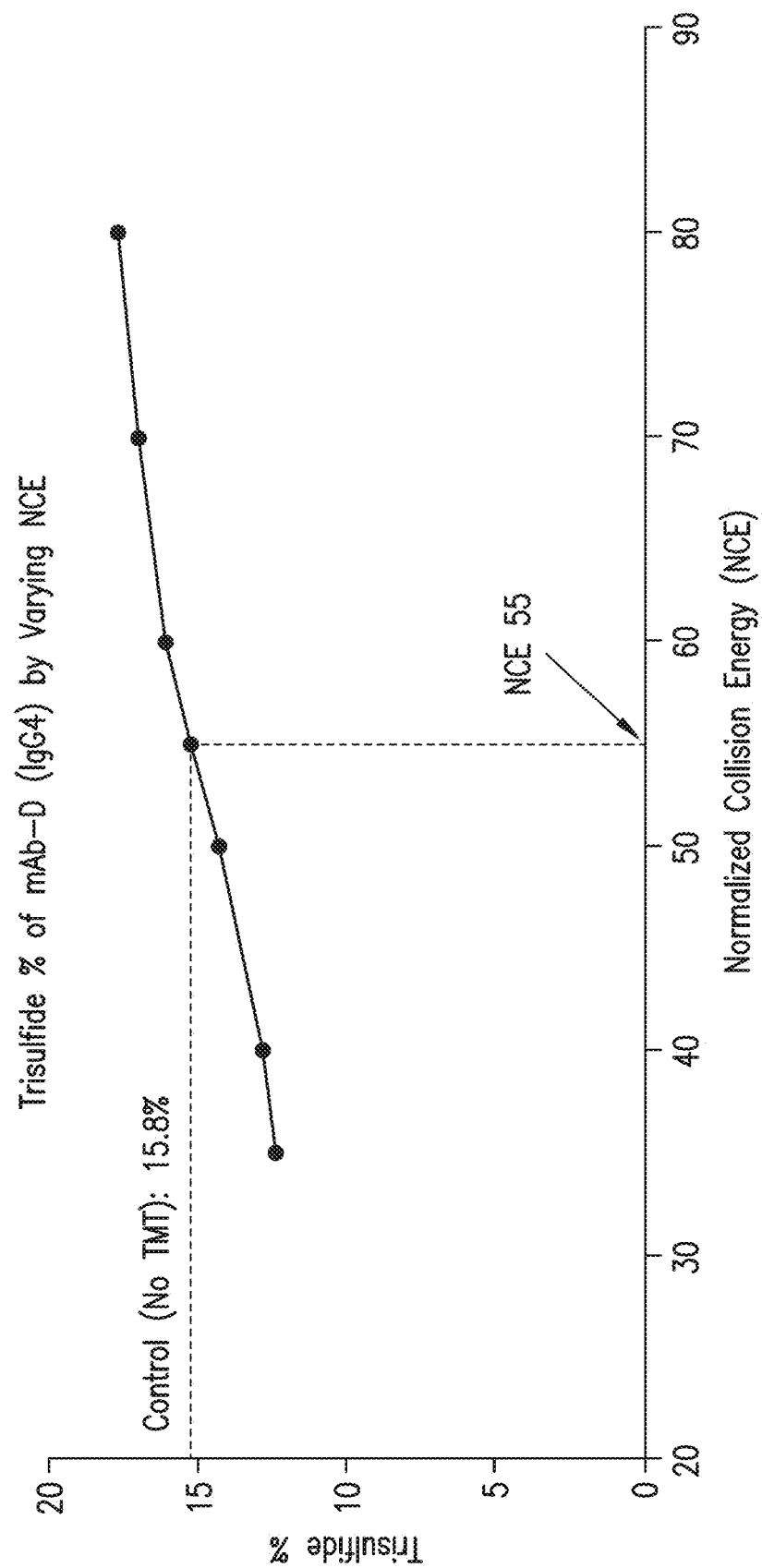

Trisulfide is also a common modification that was found to be present in all subclasses of recombinant IgGs. Trisulfide bonds are often present between the inter-light and heavy chain peptide in monoclonal antibodies (Gu et al., 2010, 400, 89-98). This trisulfide modification occurs by inserting a sulfur atom into an inter-heavy and light chain disulfide bond (Cys-S—S-Cys+$H_2$S+[0]→Cys-S—S—S-Cys+$H_2$O), resulting in a mass increase of 31.97 Da. It has been reported that the presence of trisulfide bonds has no effect on thermal stability, and antigen binding and potency. However, the trisulfide levels can be variable from lot to lot and process to process likely due to the variations of trace $H_2$S levels in the production bioreactors, therefore trisulfide levels are usually monitored in the monoclonal antibody samples during the cell culture process development. To develop a multiplexed method for trisulfide quantitation, the quantitative results at different NCEs were investigated for mAb-C (IgG1) and mAb-D (IgG4) monoclonal antibodies, respectively. Interestingly, percentages of trisulfide showed a clear linear relationship with NCEs for both Mab-C and mAb-D as demonstrated in FIGS. 3A and 3B. When NCE was increased to 55, trisulfide % quantified from this approach was comparable to the conventional approach in both IgG1 and IgG4 antibodies and therefore was selected as the optimized NCE for trisulfide quantitation.

Example 3: Small Molecule Additives to Inhibit the Over-Labeling of TMT Reagent

It has been reported that besides the N-terminal amine group and the ε-amino group of lysine side chain TMT labeling can also occur on the Tyrosine (Tyr), Threonine (Thr) and Serine (Ser) resulting from the off-target reaction with hydroxyl group in those amino acids (Zecha et al., *Mol.*

Cell. Proteomics. 2019, 18, 1468-1478). This TMT over-labeling could reduce the sensitivity of PTM quantitation in this approach by dividing the responses of the native peptide and modified peptide into multiple species labeled with different numbers of the TMT tag. For example, the inventors studies observed this in the PTM quantitation from a tryptic peptide (SEQ ID NO: 3, WQQGNVFSCSVMHEALHNHYTQK) located in the conserved CH3 domain of the heavy chain of IgGs containing a methionine residue susceptible for oxidation. After TMT labeling, a mixture of species with different TMT tags (up to 6) were observed and multiple isoforms were also observed for species containing 3, 4 and 5 TMT tags. Table 1 provided in FIG. 9 summarizes the relative abundances of species of WQQG peptide (residues 1-4 of SEQ ID NO: 3) with different TMT tags and with different isoforms. The highly heterogeneous TMT labeling of this peptide distributes the total abundance into as many as 15 different forms with relative abundances ranged from 0.2-22.0%, posing the significant challenge to quantify the Met oxidation in this peptide, especially when the level is low, by using the targeted MS/MS based approach.

To inhibit the TMT over-labeling, different TMT-to-protein (wt/wt) ratios ranging from 8:1 to 1:1 were initially investigated. Reducing the amount of TMT reagent can minimize the over-labeling, however can also increase the under-labeling of the peptide. For instance, the labeling efficiency of target peptides can be dropped from over 90% to ~35% when changing ratio from 8:1 to 1:1. Alternatively, different hydroxyl-containing small molecules (PABA, HBA, HPAA and Boc-Y) spiked into the digests during the TMT labeling were evaluated as competing reagents of those off-target amino acid residues to react with the excessive amount of TMT reagent and inhibit the over-labeling. As shown in FIG. 9, adding these small molecules indeed inhibited the TMT over-labeling of peptides to certain extent. For WQQG peptide (residues 1-4 of SEQ ID NO: 3), although the species containing 3 TMT tags is still the over-labeled product the multiple isoforms of 3 TMT labeled peptide converged into a single dominant form, comprising more than 50% of the total abundance of all species related to this peptide. The species containing 5 and 6 TMT tags were significantly suppressed with 2 and 3 TMT tags enriched instead. The similar inhibitory effect can also be seen for the other TTPP peptide, the addition of small molecules suppressed the formation of 3 TMT labeled product from 26% to <7% and enriched the expected 2 TMT labeled product up to ~94%. Although all of four small molecules demonstrated the capability of inhibiting TMT over-labeling, PABA was selected as the most suitable competing reagent by considering its higher hydrophilicity lower molecular weight compared to other small molecules, which is less likely to interfere with targeted peptides and to introduce mass spectrometry background signal.

Example 4: Reproducibility and Sensitivity of TMT Multiplexed PTM Quantitation

Figure 4A:
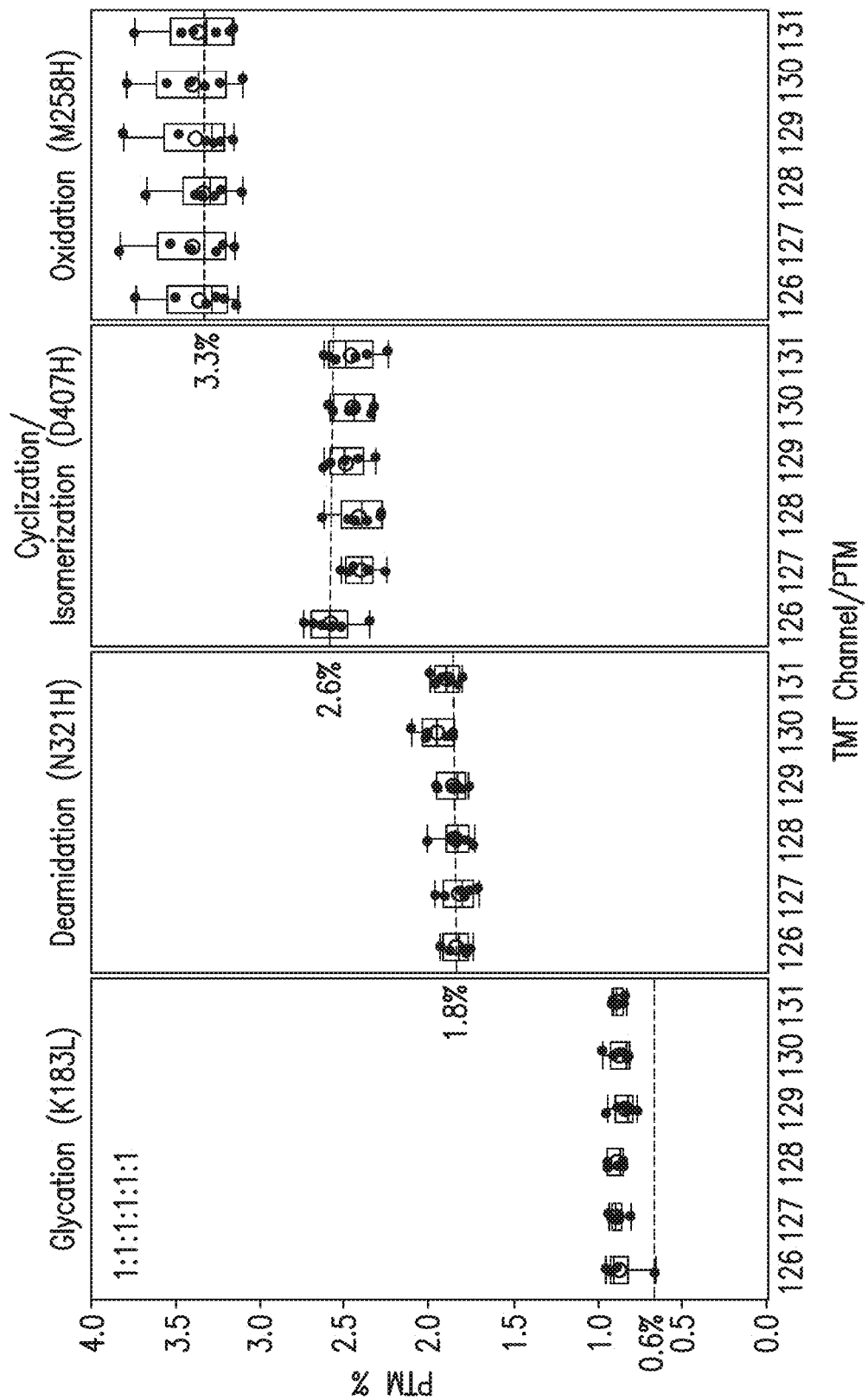
FIG. 4A shows the evaluation of the relative quantitation of four PTMs in mAb-E in six TMT channels at a ratio of 1:1:1:1:1:1. The pooled TMT-labeled samples were prepared from three determinations and analyzed by LC-MS/MS in duplicate. Box plots show the mean (larger dot), the $25^{th}$ to $75^{th}$ percentile (box), and the $5^{th}$ to $95^{th}$ percentile (whiskers). The percentages of PTMs calculated from the conventional approach are indicated by the dashed lines.
Figure 4B:
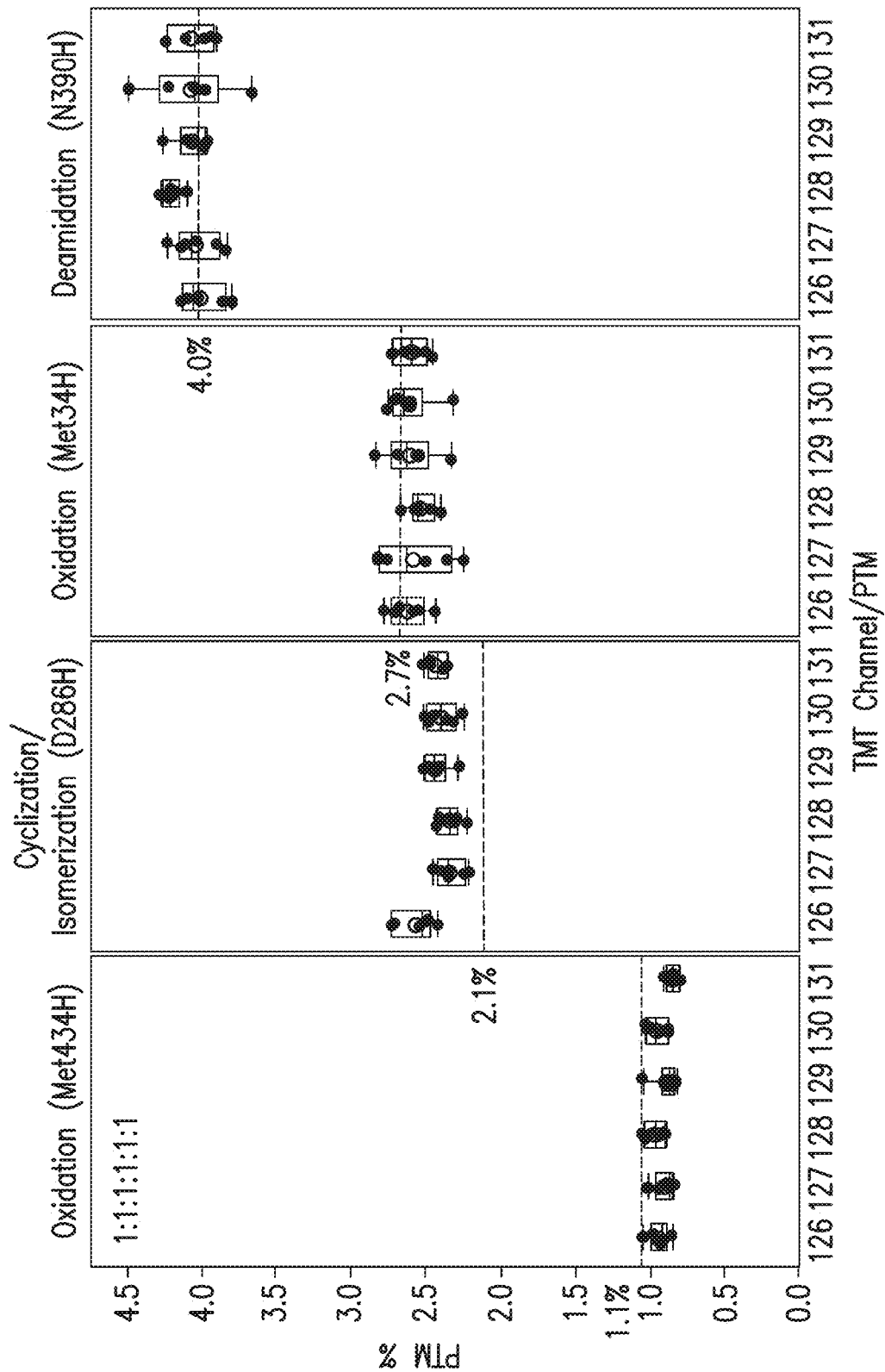
FIG. 4B shows the evaluation of reproducibility of the relative quantitation of four PTMs in mAb-E in six TMT channels at the ratio of 1:1:1:1:1:1. The pooled TMT-labeled samples were prepared from three determinations and analyzed by LC-MS/MS in duplicates. Box plots show the mean (dot), the $25^{th}$ and $75^{th}$ percentile (box), and the $5^{th}$ and $95^{th}$ percentile (whiskers). The percentages of PTMs calculated from the conventional approach are indicated by the dashed lines.

To evaluate the reproducibility and sensitivity of this targeted MS/MS based approach for PTM quantitation, each tryptic digest of the mAb-A sample from three preparations (three determinations) were aliquoted into six portions with known ratios at 1:1:1:1:1:1 and 1:2:4:8:16:32 and then labeled with 6-plex TMT tags. The three pooled samples at each ratio was analyzed twice (two replicates) by LC-MS/MS. Four representative PTMs (Lys glycation, Asn deamidation, Asp cyclization/isomerization and Met oxidation) with levels ranged from 0.6-3.3% (percentages calculated based upon conventional approach) were selected to evaluate the quantitation reproducibility and sensitivity of this approach. The integrated peak areas of extracted report ion chromatograms of the native and modified peptides were used to calculate the percentages of four PTMs in each TMT channel. In FIG. 4A, depicted is the evaluation of the relative quantitation of four PTMs in mAb-E in six TMT channels at a ratio of 1:1:1:1:1:1. FIG. 4B depicts the evaluation of reproducibility of the relative quantitation of four PTMs in mAb-E in six TMT channels at the ratio of 1:1:1:1:1:1.

Figure 5:
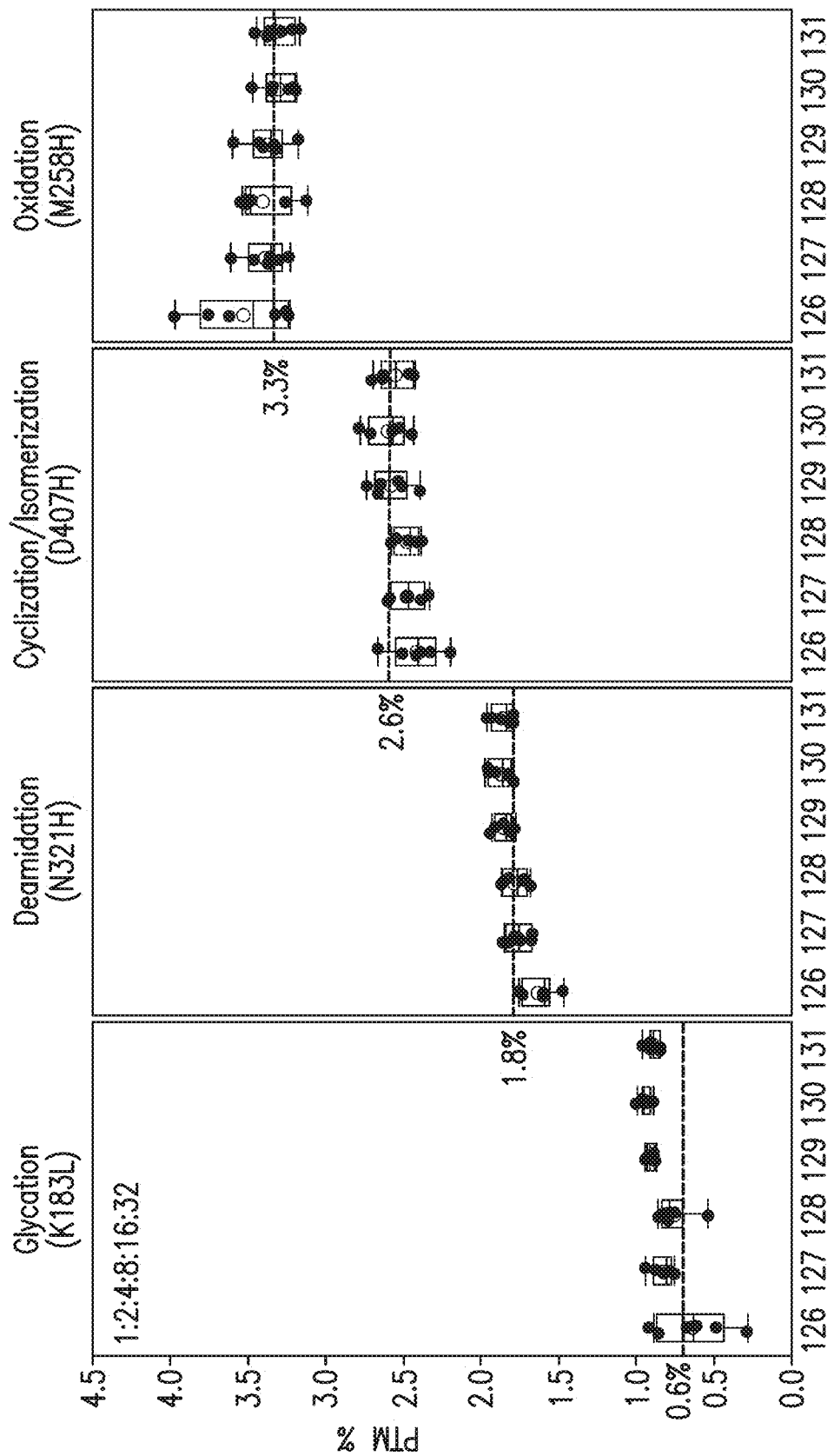
FIG. 5 shows the evaluation of sensitivity of the relative quantitation of four PTMs in mAb-A in six TMT channels at the ratio of 1:2:4:8:16:32. The pooled TMT-labeled samples were prepared from three determinations and analyzed by LC-MS/MS in duplicates. Box plots show the mean (dot), the $25^{th}$ and $75^{th}$ percentile (box), and the $5^{th}$ and $95^{th}$ percentile (whiskers). The percentages of PTMs calculated from the conventional approach are indicated by the dashed lines.

FIG. 5 shows the average percentages and RSDs of four PTMs quantified in six TMT channels at the ratio of 1:2:4:8:16:32, corresponding to the sample loading amounts of 0.15, 0.30, 0.60, 1.2, 2.4 and 4.8 µg, respectively. The average percentages and relative standard derivations (RSDs) of four PTMs quantified at different loading amounts were ranged from 0.6-0.9% and 3.3-29.0% for Lys glycation, 1.6-1.9% and 3.6-7.2% for Asn deamidation, 2.4-2.6% and 3.4-7.3% for Asp cyclization/isomerization, and 3.3-3.5% and 3.6-9.4% for Met oxidation. Overall, the average percentages of these PTMs quantified at different loading amounts were comparable to those calculated from the conventional approach (approximately 5.0 µg loading amount), even for low abundant PTM such as Lys glycation (approximately 0.6%) investigated in this study. Although when loading amount was 0.15 µg a large variation was observed with RSD of 29.0% (>15%) for quantifying this low level Lys glycation, which could be due to very low abundance of the report ion generated from the modified peptide at NCE 90, the RSDs of PTM quantitation with higher levels or larger loading amounts were all within 15%, demonstrating the high sensitivity of this approach for multiplexed PTM quantitation at levels as low as 1.0% when sample loading amount is only approximately 0.15 µg.

Example 5: TMT Multiplexed PTM Quantitation for Stability Samples of mAb-A

Figure 6:
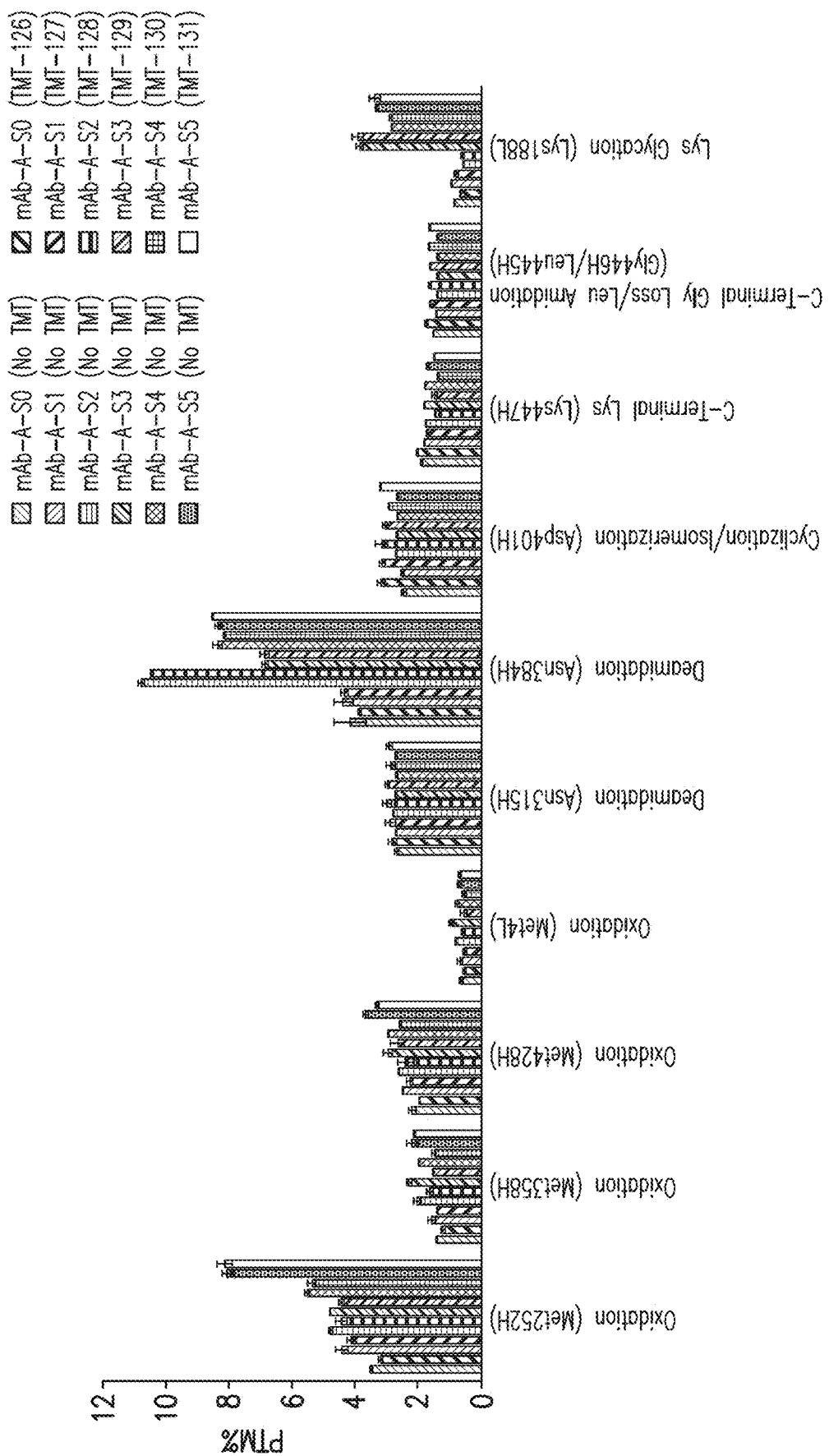
FIG. 6 shows PTM quantitation of forced degradation samples of mAb-A by the targeted MS/MS based approach (solid bars) and the conventional approach (striped bars). Black error bars: standard deviation of PTM percentages in duplicate. The ordering of bars from left to right for each site specific PTM is mAb-A-S0 (no TMT), mAb-A-S0 (TMT-126), mAb-A-S1 (no TMT), mAb-A-S1 (TMT-127), mAb-A-S2 (no TMT), mAb-A-S2 (TMT-128), mAb-A-S3 (no TMT), mAb-A-S3 (TMT-129), mAb-A-S4 (no TMT), mAb-A-S4 (TMT-130), mAb-A-S5 (no TMT), mAb-A-S5 (TMT-131).

The stability samples of mAb-A were analyzed by this targeted MS/MS based approach. A total of four samples including control sample were digested by trypsin under reducing condition and then labeled with 4-plex TMT reagents (126, 127, 128, 129, 130, and 131 channels). The pooled sample were analyzed by LC-MS/MS for PTM quantitation. The individual digested samples without TMT labeling were also analyzed by the conventional approach for PTM quantitation. FIG. 6 summarizes the multiplexed PTM quantitative results of six samples using this approach along with the results quantified in the conventional approach for comparison. Comparable results of PTM quantitation were observed in both two approaches. A temperature effect on the levels of oxidation at Met258 and Met434, deamidation at Asn390 and cyclization/isomerization at Asp286 was observed, with samples incubated at 45° C. and 25° C. exhibiting higher levels than the control sample and sample incubated at 5° C. Furthermore, slightly higher levels of these PTMs were exhibited in the sample incubated at 45° C. for 28 days than the sample incubated at 25° C. for 6 months. There was no significant difference in levels when comparing the control sample with the sample incubated at 5° C. for 24 months. For the oxidation, deamidation and cyclization/isomerization at other sites, their levels were comparable in all four samples irrespective of the stressed conditions tested in this study. This case study demonstrates the capability of this approach to quantify the difference of the PTM levels in antibody samples.

Figure 7A:
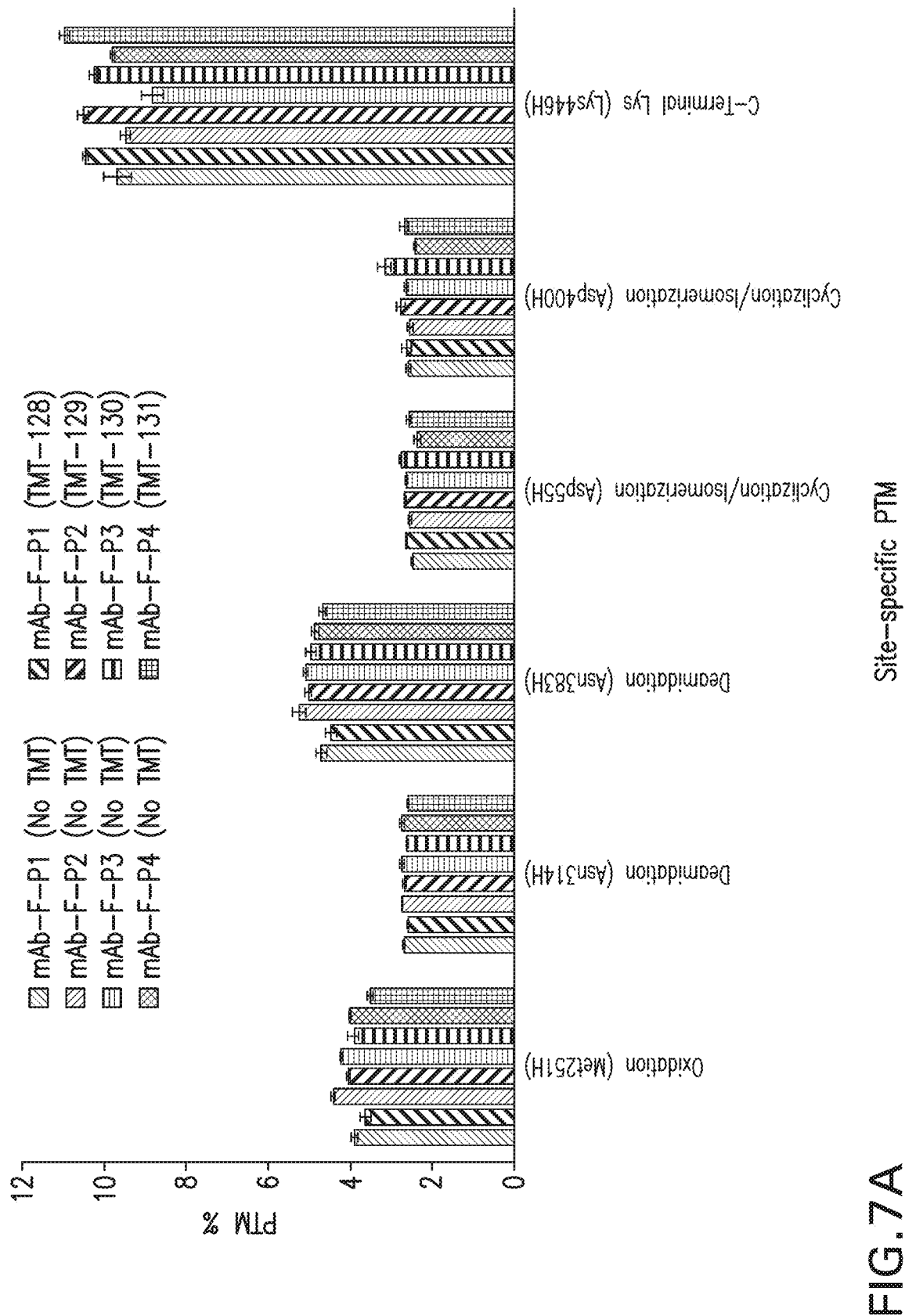
FIGS. 7A and 7B show PTM quantitation of comparability samples of mAb-F manufactured from different process areas by the targeted MS/MS based approach (solid bars) and the conventional approach (striped bars).
Figure 7B:
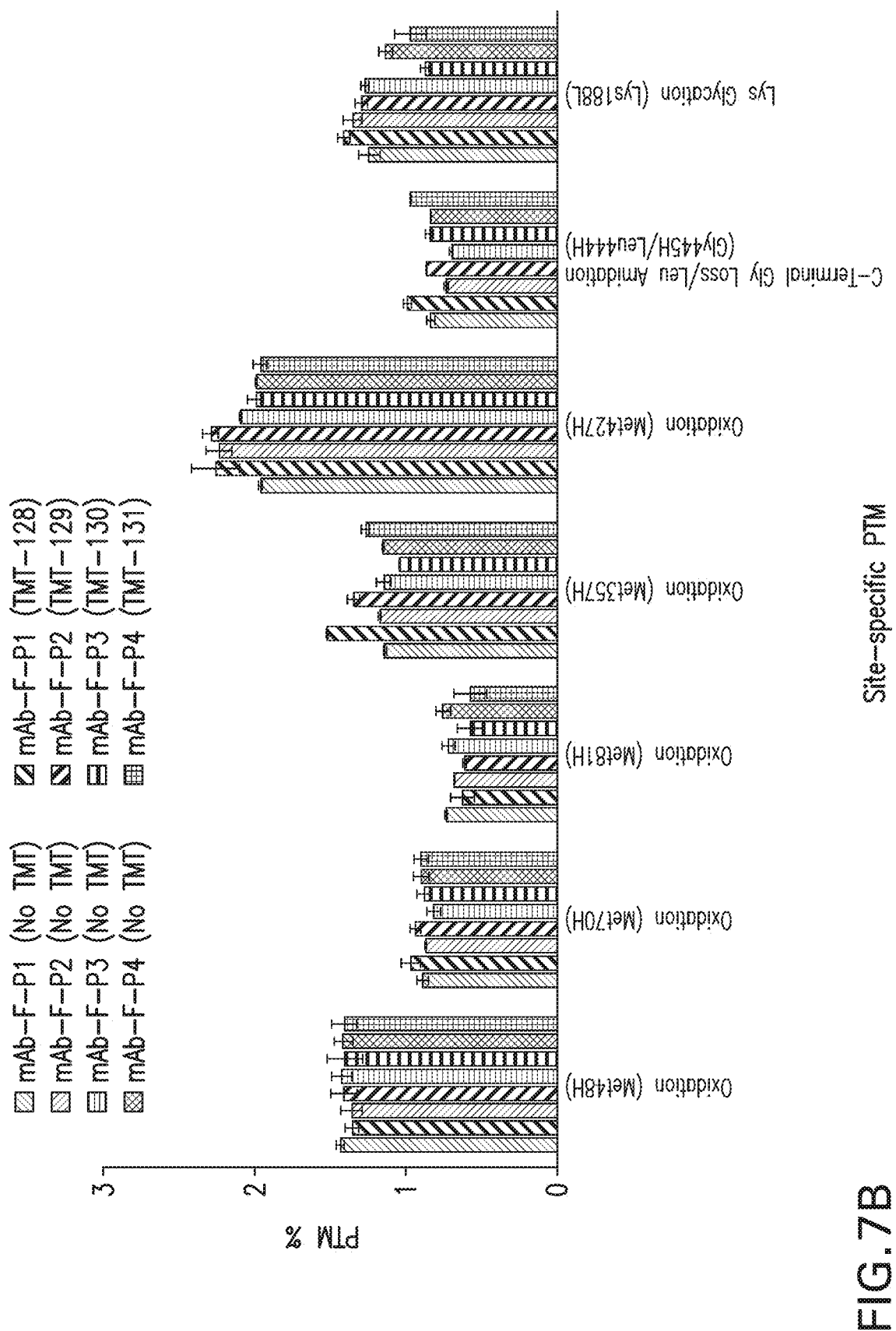

Example 6: TMT Multiplexed PTM Quantitation for Comparability Samples of mAb-B This example illustrates quantifying the PTM levels in the comparability samples of mAb-F to demonstrate the comparable quality of monoclonal antibodies manufactured from different process areas. A total of four comparability samples were digested by trypsin under reducing condition and then labeled with 4-plex TMT reagents (128, 129, 130 and 131 channels). The pooled sample were analyzed by LC-MS/MS for PTM quantitation. The individual digested samples without TMT labeling were also analyzed by the conventional approach for PTM quantitation. The PTM quantitative results of four comparability samples from both approaches are summarized in FIGS. 7A and 7B. Two approaches quantified the comparable PTM percentages, and all the PTMs including Met oxidation, Asn deamidation, Asp cyclization and isomerization and C-terminal lysine showed comparable levels in four mAb-B samples manufactured from different process areas. FIG. 7A depicts PTMs with levels>2.5% and FIG. 7B depicts PTMs with levels s 2.5%.

Figure 8:
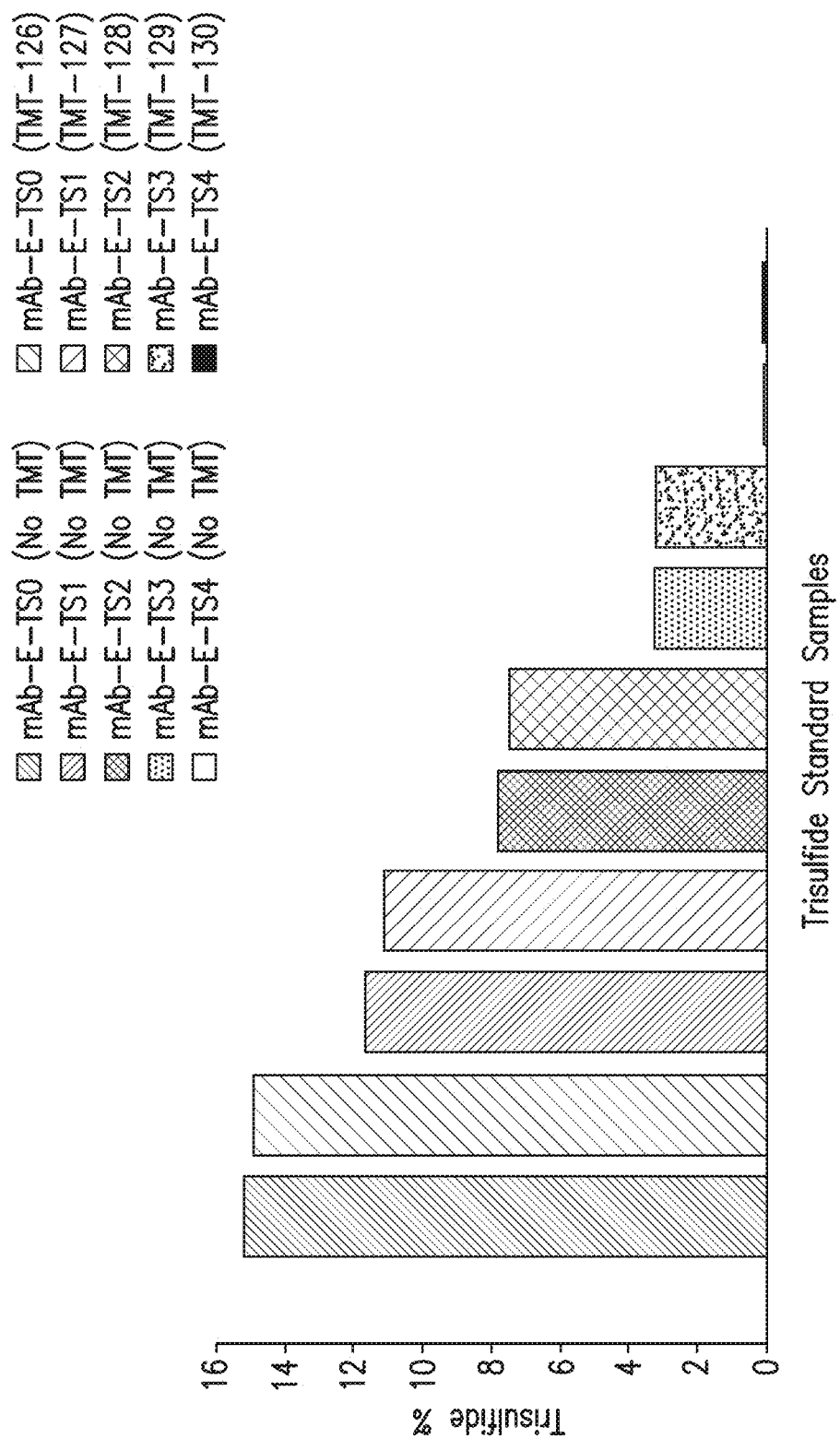
FIG. 8 shows trisulfide quantitation of trisulfide standard samples of mAb-E by the targeted MS/MS based approach (solid bars) and the conventional approach (stippled bars). mAb-E trisulfide standards with different trisulfide levels were generated by mixing $H_2S$ stressed sample and reference standard sample at different ratios. mAb-E-TS0 (100:0), mAb-E-TS1 (75:25), mAb-E-TS2 (50:50), mAb-E-TS3 (25:75) and mAb-E-TS4 (0:100).

Example 7: TMT Multiplexed PTM Quantitation for Trisulfide Standard Samples of mAb-E Trisulfide standard samples were generated to establish a calibration curve for monitoring the trisulfide levels of the in-process samples during the cell culture process development. Here we applied the targeted MS/MS based approach to quantify the trisulfide levels in five trisulfide standard samples of mAb-E generated by mixing the $H_2S$ stressed sample with reference standard sample at different ratios of 100:0, 75:25, 50:50, 25:75 and 0:100, respectively. The five trisulfide standard samples were digested by trypsin under non-reducing condition and then labeled with 5-plex TMT reagents (126, 127, 128, 129 and 130 channels). The pooled sample were analyzed by LC-MS/MS for trisulfide quantitation. The individual digested samples without TMT labeling were also analyzed by the conventional approach for comparison. As shown in FIG. 8, the trisulfide levels of standard samples quantified in this approach were 14.9%, 11.1%, 7.5%, 3.2% and 0.1%, respectively. These results were in good alignment with the values calculated based upon the mixing ratios of stressed and reference standard samples and were also comparable to the values obtained in the conventional approach, with corresponding trisulfide levels of 15.2%, 11.7%, 7.8%, 3.2% and 0.1%, respectively.

The disclosed TMT-based multiplexed approach is compatible with current peptide mapping workflow for PTM quantitation, with minimal modification on the sample preparation procedure but significantly reducing the mass spectrometry data acquisition time, especially when a large set of samples are analyzed. Herein it is demonstrated that by tuning the NCEs from 35 to 90 it is feasible to quantify different types of PTMs by the report ion generated from the native and modified peptides in the targeted MS/MS spectra with achieving comparable percentages to those in the conventional approach. It is shown that this approach offers the excellent reproducibility and sensitivity to quantify the PTMs with levels as low as 1.0% even at low sample loading amount. The multiplexing feature of this approach advances the analytical capability of LC-MS based protein biopharmaceutical characterization by quantifying the quality attributes of multiple samples in a single LC-MS run, but also reduces the run-to-run variability in the PTM quantitation which might be encountered when samples are individually analyzed by LC-MS in the conventional approach, thus improving the quality of mass spectrometry data for accurate and reproducible PTM quantitation. Overall, as demonstrated here for analysis of monoclonal antibody samples in different case studies, the developed approach provides a more efficient way compared with the conventional approach to better support ever-increasing demands for monoclonal antibody characterization at different stages of the drug development.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

---

What is claimed is:

1. A method of quantifying multiple quality attributes of multiple samples in a single mass spectrometry (MS) run, comprising:
contacting two or more samples with a digesting solution under conditions sufficient to digest the two or more samples, wherein each sample is digested separately and the digesting solution is a Tris-free buffer solution, wherein the two or more samples comprise an antibody or antigen-binding fragment thereof;
contacting each of the two or more digested samples with a small molecule additive prior to contacting each of the two or more digested samples with a specific Tandem Mass Tag (TMT) labeling reagent, wherein the small molecule additive is selected from the group consisting of BOC—Y—OH, p-Cresol, Hydroxy-phenyl acetic acid (HPAA), hydroxy benzoic acid (HBA), acetaminophen, and p-Amino Benzoic acid (PABA);
contacting each of the two or more digested samples with the TMT labeling reagent under conditions sufficient to label peptides within each of the two or more digested samples with the specific TMT labeling reagent;
quenching labeling of peptides within each of the two or more digested samples;
combining equal volumes of the two or more labeled, digested samples into a single combined sample solution; and
analyzing the single combined sample solution by targeted mass spectral analysis, thereby allowing multiple quality attributes of the two or more samples to be quantified in a single MS run.

2. The method of claim 1, wherein the multiple quality attributes comprise a post translational modification (PTM), and wherein the PTM comprises one or more of cyclization/isomerization, deamidation, oxidation, glycation, disulfide formation, N-terminal pyroglutamate formation, C-terminal lysine removal, and glycosylation.

3. The method of claim 2, wherein quantifying multiple quality attributes in a single MS run, comprises quantifying the PTM by quantifying relative abundance of PTM from extracted peak areas of a resultant report ion generated in targeted mass spectra.

4. The method of claim 1, wherein the antibody is of isotype IgG1, IgG2, IgG3, IgG4, or mixed isotype.

5. The method of claim 1, wherein two or more samples are between 2 and 11 samples.

6. The method of claim 1, further comprising preparing the two or more samples for digestion prior to contacting the two or more samples with a digesting solution under conditions sufficient to digest the two or more samples, wherein preparing the two or more samples prior to digestion comprises contacting each of the two or more samples with a denaturing and reducing solution under conditions that permit sample denaturation and reduction; and contacting each of the two or more denatured and reduced samples with an alkylating solution under conditions that permit sample alkylation.

7. The method of claim 1, wherein analyzing the single combined sample solution by targeted mass spectral analysis comprises applying the single combined sample to a separation column and performing targeted mass spectral analysis on eluted sample components.

8. The method of claim 7, wherein performing targeted mass spectral analysis on eluted sample components comprises applying electrospray ionization to generate charged ions from the eluted sample components and measuring the generated charge ions.

9. A method of quantifying post translational modifications (PTMs) of multiple samples in a single mass spectrometry (MS) run, comprising:
contacting two or more samples with a digesting solution under conditions sufficient to digest the two or more samples, wherein each sample is digested separately and the digesting solution is a Tris-free buffer solution, and wherein the two or more samples comprise an antibody or antigen-binding fragment thereof;
contacting each of the two or more digested samples with a small molecule additive;
contacting each of the two or more digested samples with a specific Tandem Mass Tag (TMT) labeling reagent under conditions sufficient to label peptides within each of the two or more digested samples with the specific TMT labeling reagent;
quenching labeling of peptides within each of the two or more digested samples;
combining equal volumes of the two or more labeled, digested samples into a single combined sample solution; and
analyzing the single combined sample solution by targeted mass spectral analysis, thereby allowing PTMs of the two or more samples to be quantified in a single MS run wherein the small molecule additive is selected from the group consisting of BOC—Y—OH, p-Cresol, Hydroxy-phenyl acetic acid (HPAA), hydroxy benzoic acid (HBA), acetaminophen, and p-Amino Benzoic acid (PABA).

10. The method of claim 9, wherein the PTMs comprise one or more of cyclization/isomerization, deamidation, oxidation, glycation, disulfide formation, N-terminal pyroglutamate formation, C-terminal lysine removal, and glycosylation.

11. The method of claim 9, wherein quantifying PTMs comprises quantifying relative abundance of PTM from extracted peak areas of a resultant report ion generated in targeted mass spectra.

12. The method of claim 9, wherein the antibody is of isotype IgG1, IgG2, IgG3, IgG4, or mixed isotype.

13. The method of claim 9, wherein two or more samples are between 2 and 16 samples.

14. The method of claim 9, further comprising preparing the two or more samples for digestion prior to contacting the two or more samples with a digesting solution under conditions sufficient to digest the two or more samples.

15. The method of claim 14, wherein preparing the two or more samples prior to digestion comprises contacting each of the two or more samples with a denaturing and reducing solution under conditions that permit sample denaturation and reduction; and contacting each of the two or more denatured and reduced samples with an alkylating solution under conditions that permit sample alkylation.

16. The method of claim 9, wherein analyzing the single combined sample solution by targeted mass spectral analysis comprises applying the single combined sample to a separation column and performing targeted mass spectral analysis on eluted sample components.

17. The method of claim 16, wherein performing targeted mass spectral analysis on eluted sample components comprises applying electrospray ionization to generate charged ions from the eluted sample components and measuring the generated charge ions.

* * * * *

SEQUENCE LISTING

```
Sequence total quantity: 4
SEQ ID NO: 1            moltype = AA  length = 22
FEATURE                 Location/Qualifiers
REGION                  1..22
                        note = Synthetic peptide sequence
source                  1..22
                        mol_type = protein
                        organism = synthetic construct
SEQUENCE: 1
GFYPSDIAVE WESNGQPENN YK                                               22

SEQ ID NO: 2            moltype = AA  length = 16
FEATURE                 Location/Qualifiers
REGION                  1..16
                        note = Synthetic peptide sequence
source                  1..16
                        mol_type = protein
                        organism = synthetic construct
SEQUENCE: 2
VVSVLTVLHQ DWLNGK                                                      16

SEQ ID NO: 3            moltype = AA  length = 23
FEATURE                 Location/Qualifiers
```

```
REGION          1..23
                note = Synthetic peptide sequence
source          1..23
                mol_type = protein
                organism = synthetic construct
SEQUENCE: 3
WQQGNVFSCS VMHEALHNHY TQK                                        23

SEQ ID NO: 4    moltype = AA  length = 17
FEATURE         Location/Qualifiers
REGION          1..17
                note = Synthetic peptide sequence
source          1..17
                mol_type = protein
                organism = synthetic construct
SEQUENCE: 4
TTPPVLDSDG SFFLYSK                                               17
```